United States Patent
Kan et al.

(10) Patent No.: US 9,330,202 B2
(45) Date of Patent: May 3, 2016

(54) EXERCISE DETECTION APPARATUS AND CONTROL METHOD FOR EXERCISE DETECTION APPARATUS

(71) Applicants: Eriko Kan, Kyoto (JP); Hideya Marukawa, Kizugawa (JP); Naoki Tsuchiya, Otsu (JP); Hiroshi Nakajima, Kyoto (JP); Yoshitake Oshima, Kyoto (JP)

(72) Inventors: Eriko Kan, Kyoto (JP); Hideya Marukawa, Kizugawa (JP); Naoki Tsuchiya, Otsu (JP); Hiroshi Nakajima, Kyoto (JP); Yoshitake Oshima, Kyoto (JP)

(73) Assignees: OMRON HEALTHCAE CO., LTD., Muko-shi (JP); OMRON CORPORATION, Kyoto-shi (JP)

( * ) Notice: Subject to any disclaimer, the term of this patent is extended or adjusted under 35 U.S.C. 154(b) by 0 days.

(21) Appl. No.: 13/711,273

(22) Filed: Dec. 11, 2012

(65) Prior Publication Data

US 2013/0123959 A1 May 16, 2013

Related U.S. Application Data

(63) Continuation of application No. PCT/JP2011/060579, filed on May 6, 2011.

(30) Foreign Application Priority Data

Jul. 16, 2010 (JP) ................................. 2010-161901

(51) Int. Cl.
*G01B 3/02* (2006.01)
*G06F 17/40* (2006.01)
(Continued)

(52) U.S. Cl.
CPC .............. *G06F 17/40* (2013.01); *A61B 5/1118* (2013.01); *A61B 5/221* (2013.01); *A61B 5/6823* (2013.01); *A61B 5/6831* (2013.01);
(Continued)

(58) Field of Classification Search
CPC ...... A61B 5/02438; A61B 5/681; A61B 5/11; A61B 5/1118
USPC .................................................... 702/141, 160
See application file for complete search history.

(56) References Cited

U.S. PATENT DOCUMENTS 6,023,662 A * 2/2000 Hayakawa ......... A61B 5/02438
600/483
2003/0208335 A1* 11/2003 Unuma ................ A43B 3/0005
702/141
(Continued)

FOREIGN PATENT DOCUMENTS

JP A-11-347021 12/1999
JP A-2005-137677 6/2005
(Continued)

OTHER PUBLICATIONS

Jun. 14, 2011 International Search Report issued in Application No. PCT/JP2011/060579 (with translation).

*Primary Examiner* — David L Lewis
*Assistant Examiner* — Eric M Thomas
(74) *Attorney, Agent, or Firm* — Oliff PLC

(57) ABSTRACT

An exercise detection apparatus determines body movements based on data detected by a detection unit, judges movement states for each body movement based on data detected by the detection unit, corrects the movement states based on a predetermined rule, calculates an exercise state of a user based on a result of the judgment, and stores the calculated exercise state in a storage unit. Accordingly, it is possible to provide an exercise detection apparatus capable of reducing erroneous judgments of the exercise states of the user.

11 Claims, 15 Drawing Sheets

(51) Int. Cl.
*A61B 5/11* (2006.01)
*A61B 5/22* (2006.01)
*A61B 5/00* (2006.01)
*G01C 22/00* (2006.01)
*A61B 5/02* (2006.01)

(52) U.S. Cl.
CPC .......... *G01C 22/006* (2013.01); *A61B 5/02042* (2013.01); *A61B 2560/0257* (2013.01); *A61B 2562/0219* (2013.01)

(56) References Cited

U.S. PATENT DOCUMENTS

2004/0176226 A1* 9/2004 Carlson .............. A63B 21/0083 482/112
2007/0072158 A1 3/2007 Unuma et al.

FOREIGN PATENT DOCUMENTS

| JP | A-2005-230340 | 9/2005 |
| JP | A-2007-093433 | 4/2007 |

* cited by examiner

FIG. 7

HUMAN ACTIVITY IDENTIFICATION

| | | WALKING DETECTED | |
|---|---|---|---|
| | ATMOSPHERIC PRESSURE CHANGE AMOUNT | YES | NO |
| ASCENDING/DESCENDING STATE — ASCENDING | HIGH $S \geq S_{th}$ | ASCENDING STAIRS | ASCENDING IN AN ELEVATOR |
| | LOW $S < S_{th}$ | | ASCENDING ON AN ESCALATOR |
| ASCENDING/DESCENDING STATE — DESCENDING | HIGH $S \geq S_{th}$ | DESCENDING STAIRS | DESCENDING IN AN ELEVATOR |
| | LOW $S < S_{th}$ | | DESCENDING ON AN ESCALATOR |
| NOT ASCENDING/ DESCENDING | | WALKING ON LEVEL GROUND | STOPPED |

FIG. 8

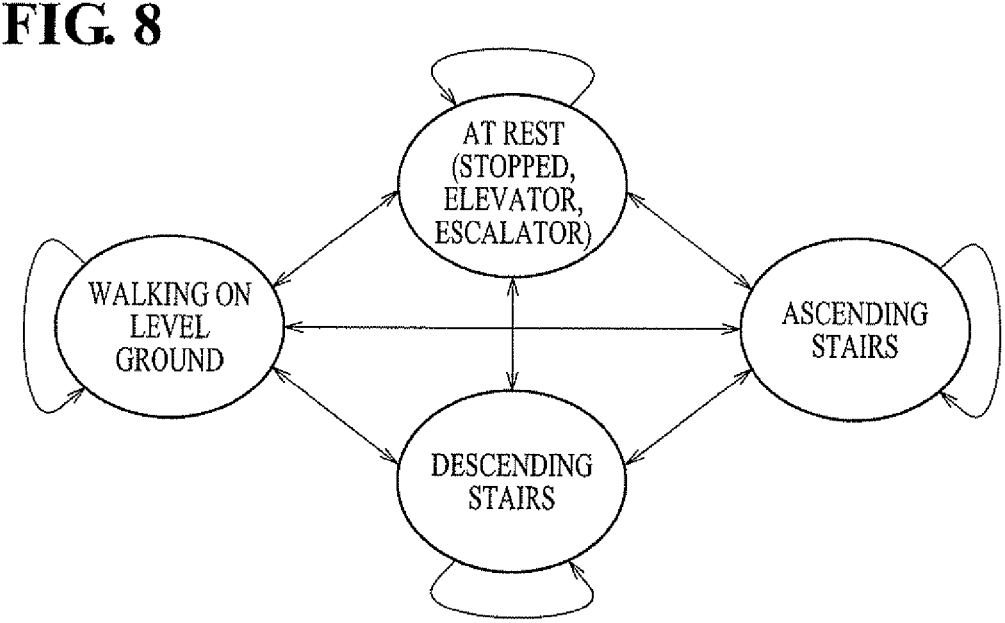

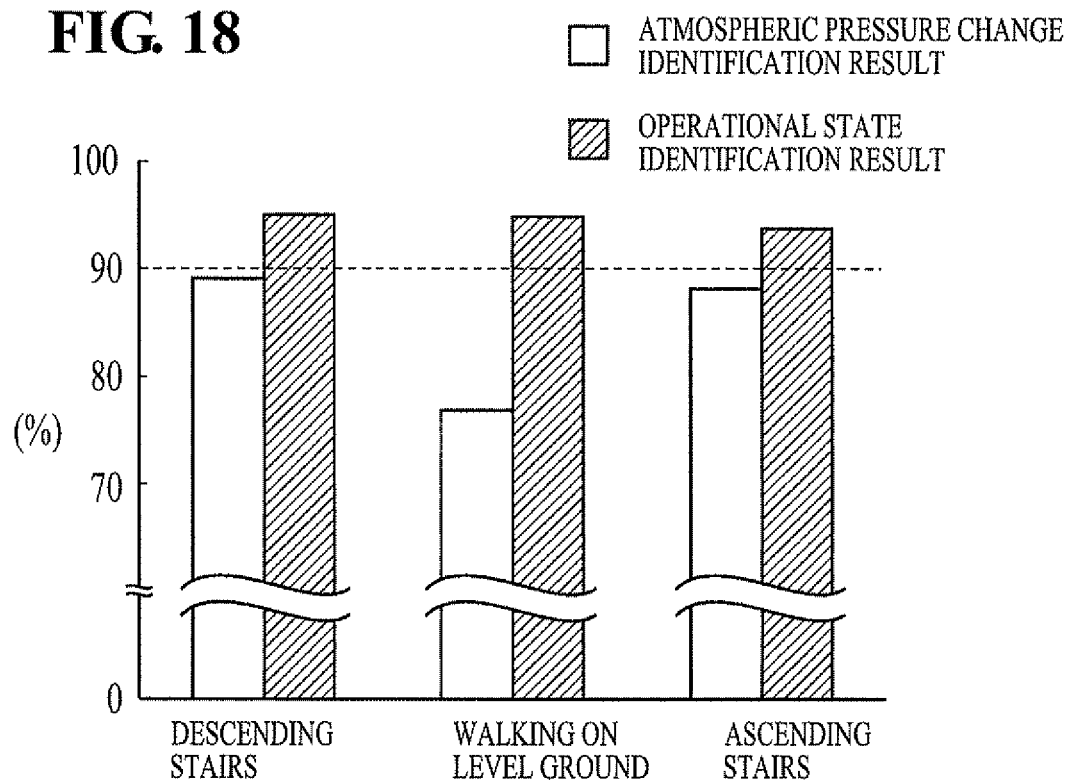

EXERCISE DETECTION APPARATUS AND CONTROL METHOD FOR EXERCISE DETECTION APPARATUS

This is a Continuation of International Application No. PCT/JP2011/060579 filed May 6, 2011, which claims the benefit of Japanese Patent Application No. 2010-161901 filed Jul. 16, 2010. The disclosure of the prior applications is hereby incorporated by reference herein in its entirety.

TECHNICAL FIELD

This invention relates to exercise detection apparatuses and control methods for exercise detection apparatuses, and particularly relates to exercise detection apparatuses and control methods for exercise detection apparatuses that are suited to calculating an exercise state with respect to walking or running.

BACKGROUND ART

Thus far, there have been apparatuses that detect changes in the acceleration of a user and changes in the atmospheric pressure resulting from movement of the user, and that obtain an energy consumption amount of the user based on the detected changes in the acceleration and atmospheric pressure (for example, see JP 2005-230340A (called "Patent Literature 1" hereinafter).

CITATION LIST

Patent Literature

Patent Literature 1: JP 2005-230340-A

SUMMARY OF INVENTION

Technical Problem

However, with an energy consumption amount estimation device as disclosed in Patent Literature 1, no measures are described as being taken with respect to erroneous judgments of exercise states of the user at various timings.

Having been achieved in order to solve the aforementioned problem, it is an object of this invention to provide an exercise detection apparatus capable of reducing erroneous judgments of exercise states of a user and a control method for such an exercise detection apparatus.

Solution to Problem

In order to achieve the aforementioned object, an exercise detection apparatus according to an aspect of this invention includes a main body unit, a control unit, a storage unit, and a detection unit. The control unit includes a first judgment unit that judges body movements based on data detected by the detection unit, a second judgment unit that judges a movement state for each of the body movements based on data detected by the detection unit, a calculation unit that calculates an exercise state of a user based on the respective judgment results from the first judgment unit and the second judgment unit, a storing unit that stores the exercise state calculated by the calculation unit in the storage unit, and a correction unit that corrects the exercise state based on a predetermined rule. The predetermined rule is a rule for correcting the exercise state based on a transition of the exercise state, and the transition occurs between the body movement that is a target of the judgment and body movement before and after the body movement that is a target of the judgment.

More preferably, the predetermined rule is a rule that, for transitions of the exercise state between the body movement that is a target of the judgment and the body movements before and after the body movement that is a target of the judgment, corrects an abnormal transition differing from a transition that can occur to a non-abnormal transition.

More preferably, for the exercise states calculated by the calculation unit for each body movement in a range of a predetermined number of body movements from before to after the body movement that is the target of judgment, the abnormal transition is a transition in the case where the exercise states of the first and last body movements are the same and body movements of an exercise state that differs from the exercise state of the first and last body movement make up less than half of the range, and the non-abnormal transition is a transition in which the exercise states of the first and last body movements are the same and the exercise states of the body movements in the range are the same.

Preferably, the exercise state is a combination of the body movement and the movement state.

Preferably, the detection unit detects an acceleration value in at least one axial direction; and of the exercise states of the user, the first judgment unit judges the body movement based on the acceleration value detected by the detection unit.

Preferably, the detection unit detects an absolute pressure value; and of the exercise states of the user, the second judgment unit calculates the movement state based on the absolute pressure value detected by the detection unit.

Preferably, the control unit further includes: an exercise intensity specification unit that specifies an exercise intensity based on the exercise states stored in the storage unit; and an exercise amount calculation unit that calculates an exercise amount using duration times of the respective exercise states stored in the storage unit and the exercise intensity specified by the exercise intensity specification unit.

A control method according to another aspect of this invention is a control method for an exercise detection apparatus that includes a main body unit, a control unit, a storage unit, and a detection unit. In the control method for the exercise detection apparatus, the control unit executes: a step of judging a body movement based on data detected by the detection unit; a step of judging a movement state for each of the body movements based on data detected by the detection unit; a step of calculating an exercise state of a user based on a result of the judgment; a step of storing the calculated exercise state in the storage unit; and a step of correcting the exercise state based on a predetermined rule. The predetermined rule is a rule for correcting the exercise state based on a transition of the exercise state, and the transition occurs between the body movement that is a target of the judgment and body movement before and after the body movement that is a target of the judgment.

Advantageous Effects of Invention

According to this invention, with the exercise detection apparatus and the control method for the exercise detection apparatus, an exercise state of a user is calculated from results of the judgment, the calculated exercise state is stored, and the exercise state is corrected based on a predetermined rule.

As a result, it is possible to provide an exercise detection apparatus capable of reducing erroneous judgments of the exercise states of the user and a control method for such an exercise detection apparatus.

BRIEF DESCRIPTION OF DRAWINGS

FIG. 7 is a diagram illustrating conditions for identification of an activity type by an activity evaluation unit in the control unit of the activity meter according to the embodiment.

FIG. 8 is a first diagram for illustrating a basic principle of correction performed by an identified activity correction unit in the control unit of the activity meter according to the embodiment.

FIG. 18 is a graph illustrating an identification rate for the operational state when using a threshold during the determination and testing of a threshold for judging the operational state.

DESCRIPTION OF EMBODIMENTS

Figure 1:
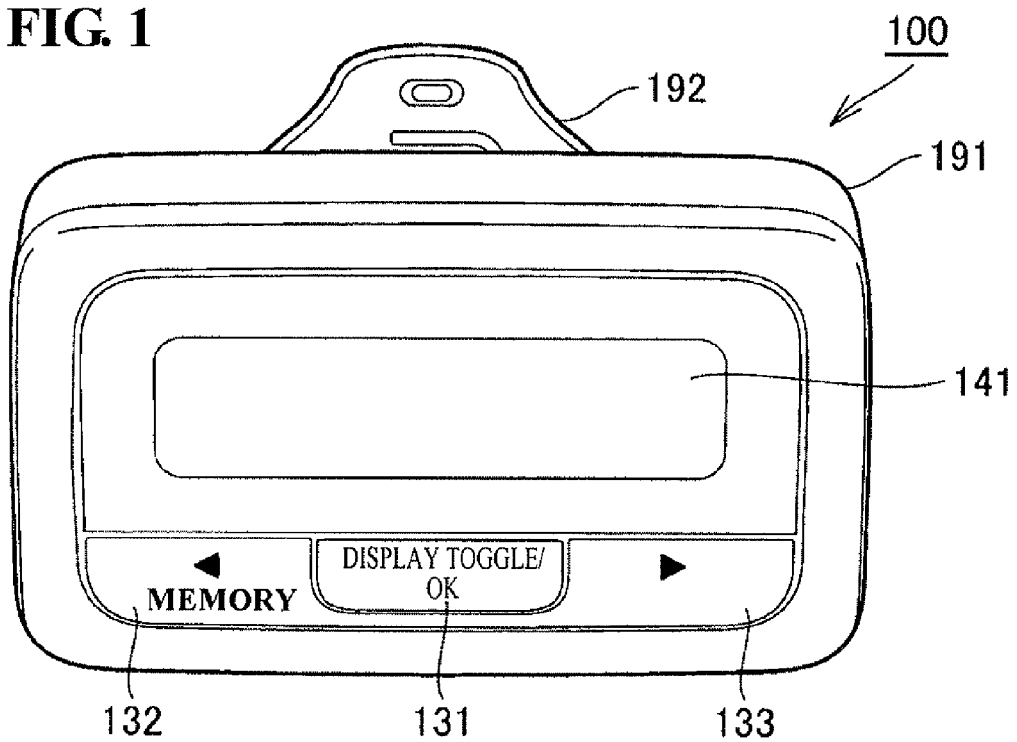
FIG. 1 is an external view of an activity meter according to an embodiment of this invention.

Hereinafter, an embodiment of this invention will be described in detail with reference to the drawings. Note that identical or corresponding elements in the diagrams will be given the same reference numerals, and descriptions thereof will not be repeated.

The present embodiment will be described assuming that an exercise detection apparatus is embodied as an activity meter capable not only of measuring a number of steps, but also of measuring an activity amount (also called an "exercise amount") during exercise and during daily activities (for example, vacuuming, carrying light objects, cooking, and so on).

FIG. 1 is an external view of an activity meter 100 according to this embodiment of the invention. As shown in FIG. 1, the activity meter 100 is primarily configured of a main body unit 191 and a clip unit 192. The clip unit 192 is used to affix the activity meter 100 to the clothing or the like of a user.

A display toggle/OK switch 131, a left operation/memory switch 132, and a right operation switch 133 that configure part of an operation unit 130, mentioned later, and a display 141 that configures part of a display unit 140, also mentioned later, are provided in the main body unit 191.

Although the display 141 is described as being configured of a liquid-crystal display (LCD) in the present embodiment, the display 141 is not limited thereto, and may be another type of display, such as an electroluminescence (EL) display.

Figure 2:
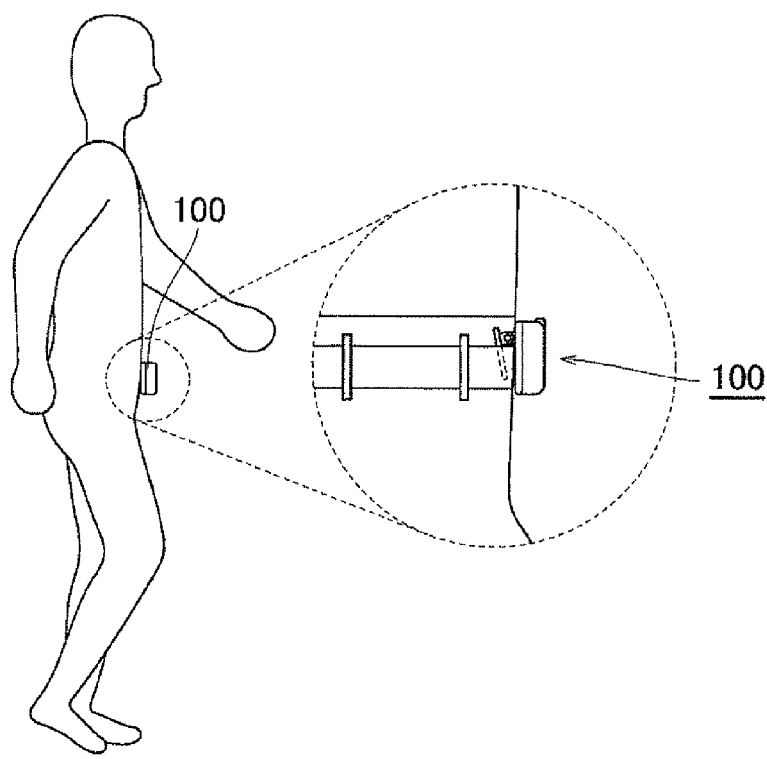
FIG. 2 is a diagram illustrating a state in which the activity meter according to the embodiment is used.

FIG. 2 is a diagram illustrating an example of a usage state of the activity meter 100 according to this embodiment. As shown in FIG. 2, the activity meter 100 is affixed to, for example, a belt around the waist of the user using the clip unit 192.

Note that the activity meter 100 is not limited to this configuration, and may be designed to be affixed to another part of the user's body, or to be used when inserted into an carried in the user's purse or the like.

Figure 3:
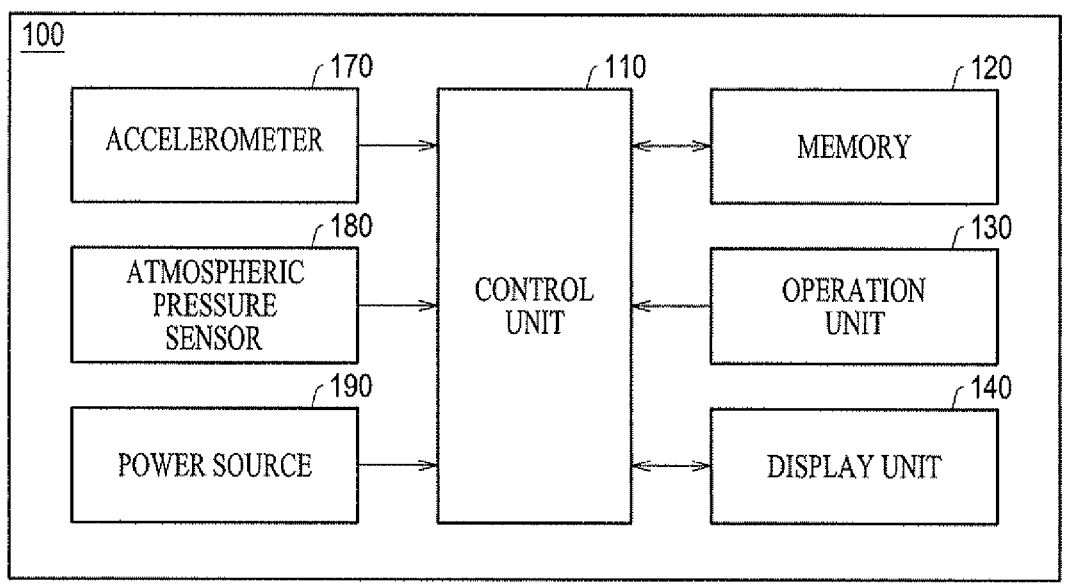
FIG. 3 is a block diagram illustrating the overall configuration of the activity meter according to the embodiment.

FIG. 3 is a block diagram illustrating the overall configuration of the activity meter 100 according to this embodiment. As shown in FIG. 3, the activity meter 100 includes a control unit 110, a memory 120, the operation unit 130, the display unit 140, an accelerometer 170, an atmospheric pressure sensor 180, and a power source 190. In addition, the activity meter 100 may include an alarm unit for outputting a sound, an interface for communicating with an external computer, and so on.

The control unit 110, the memory 120, the operation unit 130, the display unit 140, the accelerometer 170, the atmospheric pressure sensor 180, and the power source 190 are contained within the main body unit 191 illustrated in FIG. 1.

The operation unit 130 includes the display toggle/OK switch 131, the left operation/memory switch 132, and the right operation switch 133 illustrated in FIG. 1, and sends operation signals indicating that those switches have been manipulated to the control unit 110.

Although a semiconductor-based element that uses a MEMS (micro-electromechanical system) technique is employed as the accelerometer 170, the accelerometer 170 is not limited thereto, and may employ a different system, such as a mechanical system or an optical system. In the present embodiment, the accelerometer 170 outputs, to the control unit 110, detection signals indicating accelerations in each of three axial directions. However, the accelerometer 170 is not limited to three axes, and may employ one axis or two axes.

Although a MEMS-based element is used as the atmospheric pressure sensor 180, the atmospheric pressure sensor 180 is not limited thereto, and may be an element that uses a different system. The atmospheric pressure sensor 180 outputs, to the control unit 110, a detection signal indicating a surrounding atmospheric pressure value (an absolute pressure, in the present embodiment).

The memory 120 includes a non-volatile memory such as a ROM (read-only memory) (for example, a flash memory) and a volatile memory such as a RAM (random access memory) (for example, and SDRAM (synchronous dynamic random access memory)).

The memory 120 stores data of programs for controlling the activity meter 100, data used for controlling the activity meter 100, configuration data for configuring various types of functions of the activity meter 100, and data of results of measuring a number of steps, an activity amount, and so on in each of predetermined amount of times (for example, for each day). The memory 120 is also used as a working memory when programs are executed.

The control unit 110 includes a CPU (central processing unit), and controls, in accordance with a program for controlling the activity meter 100 stored in the memory 120, the memory 120 and the display unit 140 based on the detection signals from the accelerometer 170 and the atmospheric pressure sensor 180, in response to an operation signal from the operation unit 130.

The display unit 140 includes the display 141 illustrated in FIG. 1, and control is carried out so that predetermined information is displayed in the display 141 in accordance with a control signal from the control unit 110.

The power source 190 includes a replaceable battery, and supplies electrical power from the battery to various units of the activity meter 100 that require electrical power to operate, such as the control unit 110.

Figure 4:
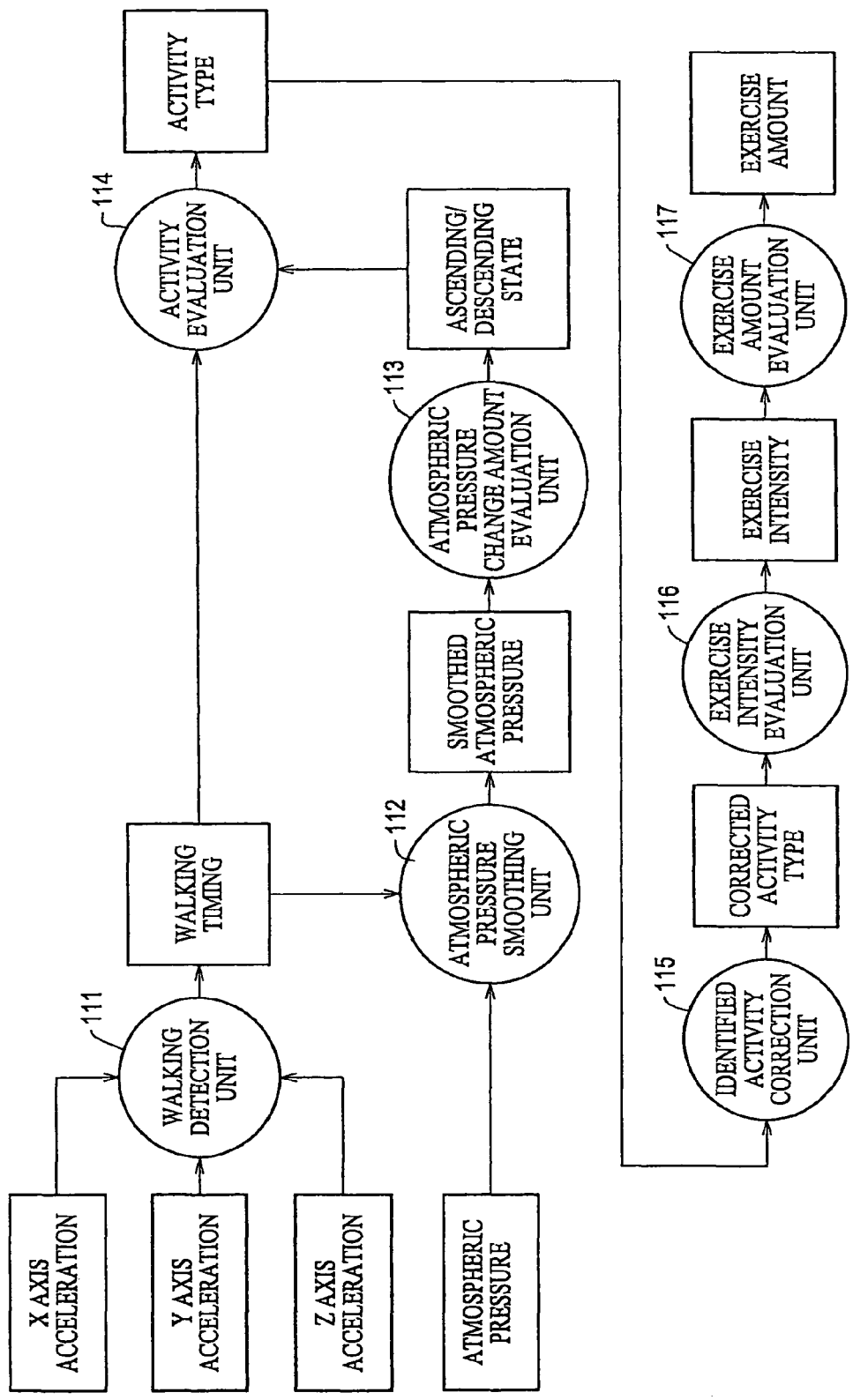
FIG. 4 is a functional block diagram illustrating the overall functions of the activity meter according to the embodiment.

FIG. 4 is a function block diagram illustrating the overall functions of the activity meter 100 according to this embodiment. As shown in FIG. 4, the control unit 110 of the activity meter 100 includes a walking detection unit 111, an atmospheric pressure smoothing unit 112, an atmospheric pressure change amount evaluation unit 113, an activity evaluation unit 114, an identified activity correction unit 115, an exercise intensity evaluation unit 116, and an exercise amount evaluation unit 117.

Note that in the present embodiment, it is assumed that these respective units included in the control unit 110 are configured in the control unit 110 by the control unit 110 executing software for executing the processes illustrated in FIGS. 5 through 9, mentioned later.

However, the embodiment is not limited thereto, and the respective units included in the control unit 110 may be configured within the control unit 110 as hardware circuitry.

The walking detection unit 111 detects walking of the user that is wearing or carrying the activity meter 100, based on accelerations in the three axial directions from the accelerometer 170, or in other words, values for an X axis acceleration, a Y axis acceleration, and a Z axis acceleration. The walking detection unit 111 then outputs a timing of the detected walking to the atmospheric pressure smoothing unit 112 and the activity evaluation unit 114.

In the case where walking has not been detected, the walking detection unit 111 notifies the atmospheric pressure smoothing unit 112 and the activity evaluation unit 114 thereof every predetermined amount of time T (for example, 1 second).

Based on a value P of the atmospheric pressure from the atmospheric pressure sensor 180 and the timing of the walking from the walking detection unit 111, the atmospheric pressure smoothing unit 112 calculates an average value of atmospheric pressure values in a five-step range from two steps before to two steps after a target judgment timing as a smoothed atmospheric pressure $P_{ma}$, for each target judgment timing. Here, the target judgment timing is every one step of the timing of the walking.

In the case where the atmospheric pressure smoothing unit 112 has been notified that walking is not being detected by the walking detection unit 111, the atmospheric pressure smoothing unit 112 calculates an average value of atmospheric pressure values in a 4T-second range from 2T seconds before to 2T seconds after the target judgment timing as the smoothed atmospheric pressure $P_{ma}$, for each target judgment timing every T seconds.

Although the average value of atmospheric pressures within a five-step (4T-second) range is calculated here, it should be noted that the configuration is not limited thereto, and the range for which to calculate the average value may be a range $M_{frame}$ (steps) (where $M_{frame}$ is a natural number).

In addition, although the smoothed atmospheric pressure is described as being calculated every one step (T seconds), the configuration is not limited thereto, and the smoothed atmospheric pressure may be calculated every $N_{frame}$ (steps) (where $N_{frame}$ is a natural number).

Figure 5:
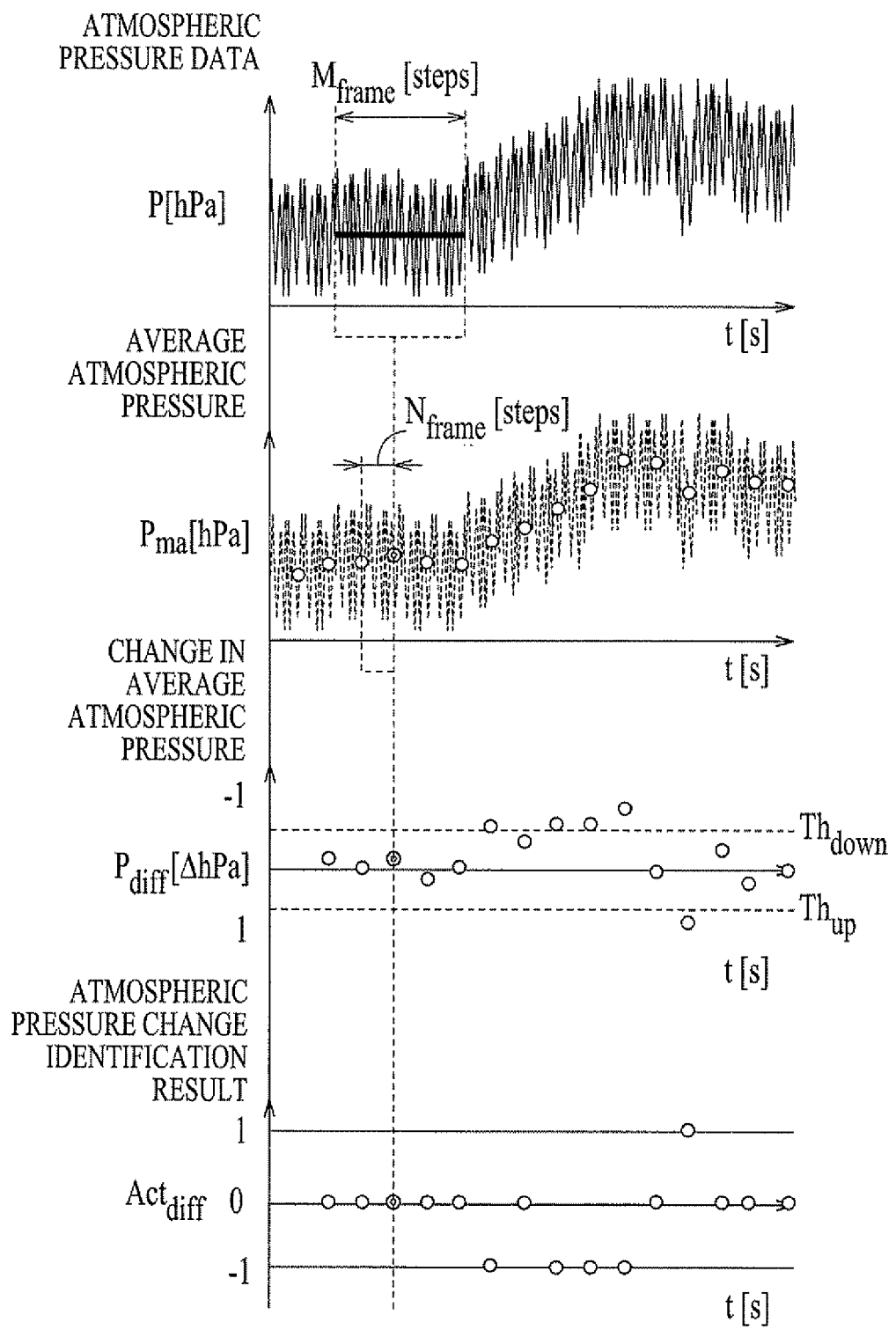
FIG. 5 is a graph illustrating an example of processes carried out by an atmospheric pressure smoothing unit and an atmospheric pressure change amount evaluation unit in a control unit of the activity meter according to the embodiment.

FIG. 5 is a graph illustrating an example of processes carried out by the atmospheric pressure smoothing unit 112 and the atmospheric pressure change amount evaluation unit 113 in the control unit 110 of the activity meter 100 according to this embodiment. As shown in FIG. 5, the horizontal axis of the four graphs represents a time t (s). The vertical axis in the graph on the first level expresses changes in an atmospheric pressure value P (hPa) inputted into the control unit 110 from the atmospheric pressure sensor 180.

The vertical axis in the graph on the second level expresses changes in the smoothed atmospheric pressure $P_{ma}$ (hPa). An average value of a range $M_{frame}$=five steps in the graph on the first level is calculated by the atmospheric pressure smoothing unit 112 as the smoothed atmospheric pressure $P_{ma}$ indicated by the plots in the graph on the second level.

Returning to FIG. 4, the atmospheric pressure change amount evaluation unit 113 calculates, based on the smoothed atmospheric pressure from the atmospheric pressure smoothing unit 112, a change amount $P_{diff}$ (hPa) expressing a change from the smoothed atmospheric pressure one step prior to the target judgment timing to the smoothed atmospheric pressure at the target judgment timing.

In the case where walking is not being detected, the atmospheric pressure change amount evaluation unit 113 calculates, based on the smoothed atmospheric pressure from the atmospheric pressure smoothing unit 112, the change amount $P_{diff}$ (hPa) expressing a change from the smoothed atmospheric pressure a predetermined amount of time T seconds prior to the target judgment timing to the smoothed atmospheric pressure at the target judgment timing.

Moving to FIG. 5, the vertical axis in the graph on the third level expresses changes in the change amount $P_{diff}$. In the graph on the third level, thresholds $Th_{up}$ and $Th_{down}$ are thresholds, for the smoothed atmospheric pressure change amount $P_{diff}$, for walking on level ground or stopping and ascending or descending, for each step. In the present embodiment, it is assumed that $Th_{up}=-0.01$ and $Th_{down}=0.01$.

Returning to FIG. 4, in the case where the change amount $P_{diff}$ at the target judgment timing is less than the threshold $Th_{up}$, the atmospheric pressure change amount evaluation unit 113 takes the value of an atmospheric pressure change identification result $Act_{diff}$ as 1, or in other words, takes the operational state at the target judgment timing as an operational state that is highly likely to be ascending.

Meanwhile, in the case where the change amount $P_{diff}$ at the target judgment timing is greater than or equal to the threshold $Th_{up}$ but less than or equal to the threshold $Th_{down}$, the atmospheric pressure change amount evaluation unit 113 takes the value of the atmospheric pressure change identification result $Act_{diff}$ as 0, or in other words, takes the operational state at the target judgment timing as an operational state that is highly likely to be walking on level ground or stopped.

Furthermore, in the case where the change amount $P_{diff}$ at the target judgment timing is greater the threshold $Th_{down}$, the atmospheric pressure change amount evaluation unit 113 takes the value of the atmospheric pressure change identification result $Act_{diff}$ as −1, or in other words, takes the operational state at the target judgment timing as an operational state that is highly likely to be descending.

Moving to FIG. 5, the vertical axis in the graph on the fourth level expresses changes in the atmospheric pressure change identification result $Act_{diff}$. In the graph on the third level, the first through fifth, eleventh, and thirteenth through fifteenth plots are within a range that is greater than or equal to the threshold $Th_{up}$ and less than or equal to the threshold $Th_{down}$, and thus in the graph on the fourth level, values of the atmospheric pressure change identification result $Act_{diff}$ corresponding to these plots are 0.

In the graph on the third level, the sixth and eighth through tenth plots are within a range that is greater than the threshold $Th_{down}$, and thus in the graph on the fourth level, values of the atmospheric pressure change identification result $Act_{diff}$ corresponding to these plots are −1.

In the graph on the third level, the twelfth plot is within a range that is less than the threshold $Th_{up}$, and thus in the graph on the fourth level, the value of the atmospheric pressure change identification result $Act_{diff}$ corresponding to this plot is 1.

Returning to FIG. 4, based on the atmospheric pressure change identification result $Act_{diff}$, the atmospheric pressure change amount evaluation unit 113 calculates an average value for a five-step range from two steps before to two steps after the target judgment timing as an identification result movement average $Act_{ma}$, for each target judgment timing, or in other words, for each step in the timing of the walking.

In the case where walking is not being detected, the atmospheric pressure change amount evaluation unit 113 calculates an average value for a 4T-second range from 2T seconds before to 2T seconds after the timing of the target for judgment as the identification result movement average $Act_{ma}$, for each timing of the target for judgment every T seconds.

Figure 6:
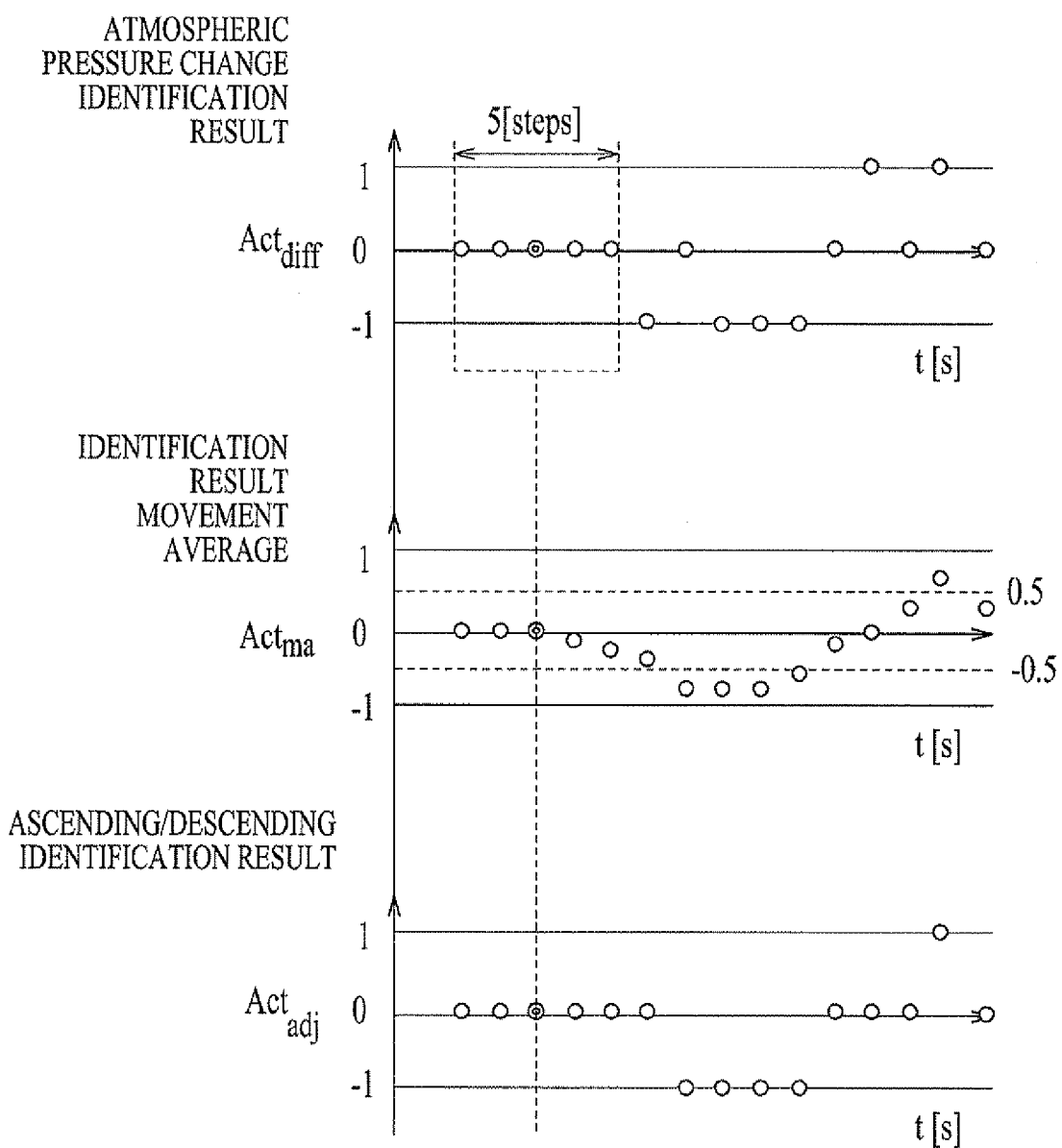
FIG. 6 is a graph illustrating a continuation of the example of processes carried out by the atmospheric pressure change amount evaluation unit in the control unit of the activity meter according to the embodiment.

FIG. 6 is a graph illustrating a continuation of the example of processes carried out by the atmospheric pressure change amount evaluation unit 113 in the control unit 110 of the activity meter according to this embodiment. As shown in FIG. 6, the horizontal axis of the three graphs represents a time t (s). The graph on the first level is the same as the graph on the fourth level in FIG. 5.

The vertical axis of the graph on the second level expresses changes in the identification result movement average $Act_{ma}$. An average value in a five-step range in the graph on the first level is calculated by the atmospheric pressure change amount evaluation unit 113 as the identification result movement average $Act_{ma}$ indicated by the plots in the graph on the second level.

Returning to FIG. 4, in the case where the identification result movement average $Act_{ma}$ at the target judgment timing is greater than a threshold of 0.5, the atmospheric pressure change amount evaluation unit 113 takes the value of an ascending/descending state identification result $Act_{adj}$ as 1, or in other words, takes an ascending/descending state prior to the correction of the target judgment timing as ascending. Note that the threshold for the identification result movement average $Act_{ma}$ is not limited to 0.5, and may be another value.

Meanwhile, in the case where the identification result movement average $Act_{ma}$ at the target judgment timing is less than or equal to the threshold of −0.5 and greater than or equal to a threshold of −0.5, the atmospheric pressure change amount evaluation unit 113 takes the value of the ascending/descending state identification result $Act_{adj}$ as 0, or in other words, takes the ascending/descending state prior to the correction of the target judgment timing as not ascending/descending.

Meanwhile, in the case where the identification result movement average $Act_{ma}$ at the target judgment timing is less than the threshold of −0.5, the atmospheric pressure change amount evaluation unit 113 takes the value of the ascending/descending state identification result $Act_{adj}$ as −1, or in other words, takes the ascending/descending state prior to the correction of the target judgment timing as descending.

Moving to FIG. 6, the vertical axis in the graph on the third level expresses changes in the ascending/descending state identification result $Act_{adj}$. In the graph on the second level, the first through sixth, eleventh through thirteenth, and fifteenth plots are within a range that is less than or equal to the threshold 0.5 and greater than or equal to the threshold −0.5, and thus in the graph on the third level, the values of the ascending/descending state identification result $Act_{adj}$ that correspond to these plots are set to 0.

In the graph on the second level, the seventh through tenth plots are within a range that is less than the threshold −0.5, and thus in the graph on the third level, the values of the ascending/descending state identification result $Act_{adj}$ that correspond to these plots are set to −1.

In the graph on the second level, the fourteenth plot is within a range that is greater than the threshold 0.5, and thus in the graph on the third level, the value of the ascending/descending state identification result $Act_{adj}$ that corresponds to this plot is set to 1.

Returning to FIG. 4, the activity evaluation unit 114 identifies the operational state (also called the "activity type") based on the timing of walking, or a lack of detection of walking, from the walking detection unit 111 and the ascending/descending state identification result $Act_{adj}$ from the atmospheric pressure change amount evaluation unit 113.

FIG. 7 is a diagram illustrating conditions for identification of an activity type by the activity evaluation unit 114 in the control unit 110 of the activity meter 100 according to this embodiment. As shown in FIG. 7, in the case where the atmospheric pressure change amount evaluation unit 113 has identified that the ascending/descending state is ascending with respect to the operational state at the target judgment timing, the operational state is identified as ascending stairs in the case where walking is detected.

On the other hand, in the ease where walking is not detected, the activity type is identified as ascending in an elevator if an atmospheric pressure change amount S from a predetermined amount of time prior to the target judgment timing is high, or in other words, is greater than or equal to a threshold $S_{th}$, and is identified as ascending in an escalator if the change amount S is low, or in other words, is less than the threshold $S_{th}$.

In the case where the atmospheric pressure change amount evaluation unit 113 has identified that the ascending/descending state is descending with respect to the operational state at the target judgment timing, the operational state is identified as descending stairs in the case where walking is detected.

On the other hand, in the case where walking is not detected, the activity type is identified as descending in an elevator if the atmospheric pressure change amount S from the predetermined amount of time prior to the target judgment timing is high, or in other words, is greater than or equal to the threshold $S_{th}$, and is identified as descending in an escalator if the change amount S is low, or in other words, is less than the threshold $S_{th}$.

In the case where the atmospheric pressure change amount evaluation unit 113 has identified that the ascending/descending state is not ascending/descending with respect to the operational state at the target judgment timing, the operational state is identified as walking on level ground in the case where walking is detected. Meanwhile, in the case where walking is not detected, the user is identified as being stopped,

TABLE 1

| | | WALKING STATE | |
|---|---|---|---|
| | | 0 | 1 |
| ASCENDING/ DESCENDING STATE | 2 | ASCENDING IN ELEVATOR | |
| | 1 | ASCENDING ON ESCALATOR | ASCENDING STAIRS |
| | 0 | STOPPED | WALKING ON LEVEL GROUND |
| | −1 | DESCENDING ON ESCALATOR | DESCENDING STAIRS |
| | −2 | DESCENDING IN ELEVATOR | |

As shown in Table 1, in the case were walking is detected, a walking state is set to 1. In the case where, when the walking state is 1, the activity type is identified as ascending stairs, the ascending/descending state is set to 1; in the case where the activity type is identified as descending stairs, the ascending/descending state is set to −1; and in the case where the activity type has been identified as walking on level ground, the ascending/descending state is set to 0.

Meanwhile, in the case where walking is not detected, the walking state is set to 0. When the walking state is 0, the ascending/descending state is set to 2 in the case where the activity type has been identified as ascending in an elevator; the ascending/descending state is set to 1 in the case where the activity type has been identified as ascending on an escalator; the ascending/descending state is set to 0 in the case where the user is identified as being stopped; the ascending/descending state is set to −1 in the case where the activity type has been identified as descending on an escalator; and the ascending/descending state is set to −2 in the case where the activity type has been identified as descending in an elevator.

Returning to FIG. 4, the identified activity correction unit 115 corrects the activity type based on the activity type (operational state) at each target judgment timing from the activity evaluation unit 114.

Figure 9:
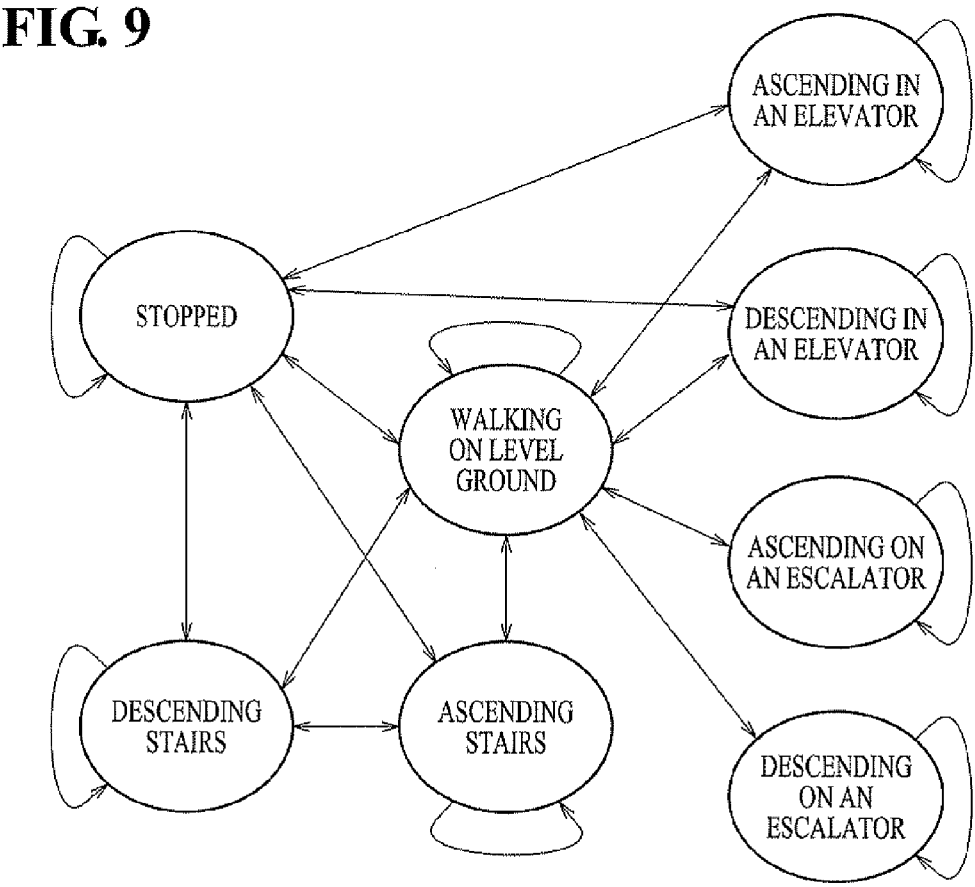
FIG. 9 is a second diagram for illustrating a basic principle of correction performed by the identified activity correction unit in the control unit of the activity meter according to the embodiment.

FIG. 8 is a first diagram for illustrating a basic principle of correction performed by the identified activity correction unit 115 in the control unit 110 of the activity meter 100 according to the embodiment. FIG. 9 is a second diagram for illustrating a basic principle of correction performed by the identified activity correction unit 115 in the control unit 110 of the activity meter 100 according to the embodiment.

As shown in FIGS. 8 and 9, in the case where the operational state is "walking on level ground", the next instance of the operational state can transition to the same operational state ("walking on level ground"), "at rest (stopped, ascending/descending in an elevator, ascending/descending on an escalator)", "ascending stairs", or "descending stairs".

In the case where the operational state is "ascending stairs", the next instance of the operational state can transition to the same operational state ("ascending stairs"), "at rest (stopped)", "walking on level ground", or "descending stairs".

In the case where the operational state is "descending stairs", the next instance of the operational state can transition to the same operational state ("descending stairs"), "at rest (stopped)", "walking on level ground", or "ascending stairs".

In the case where the operational state is "at rest (stopped)", the next instance of the operational state can transition to the same operational state ("at rest (stopped, ascending in an elevator, descending in an elevator)", "walking on level ground", "ascending stairs", or "descending stairs".

In the case where the operational state is "at rest (ascending in an elevator)", the next instance of the operational state can transition to the same operational state ("at rest (stopped, ascending in an elevator)") or "walking on level ground".

In the case where the operational state is "at rest (descending in an elevator)", the next instance of the operational state can transition to the same operational state ("at rest (stopped, descending in an elevator)") or "walking on level ground".

In the case where the operational state is "at rest (ascending on an escalator)", the next instance of the operational state can transition to the same operational state ("at rest (ascending on an escalator)") or "walking on level ground".

In the case where the operational state is "at rest (descending on an escalator)", the next instance of the operational state can transition to the same operational state ("at rest (descending on an escalator)") or "walking on level ground".

In the present embodiment, an operational state transition in the case where, in a range of a given predetermined number of units of walking, the operational states are the same in the first and last units of walking and there are less units of walking in an operational state that is different from the operational state in the first and last units of walking than half the units of walking contained in that range, is assumed to be an abnormal transition.

Thus a rule is determined for correcting this abnormal transition to a non-abnormal transition, in which in a range of a given predetermined number of units of walking, the operational states are the same in the first and last units of walking and the operational states of the units of walking contained in that range are the same.

Specifically, the following holds true when the unit of walking is assumed to be one step and the predetermined number is five steps. An operational state transition in the case where in a five-step range, the operational states of the first step and the fifth step (walking on level ground, ascending stairs, or descending stairs) are the same and an operational state that is different from the operational state in the first step and the fifth step in the continues for less than 2.5 steps (greater than or equal to one step) is present is assumed to be an abnormal transition.

Thus a rule is determined for correcting this abnormal transition to a non-abnormal transition, in which in a five-step range, the operational states are the same in the first step and the fifth step and the operational states contained in that range are the same.

Figure 10A:
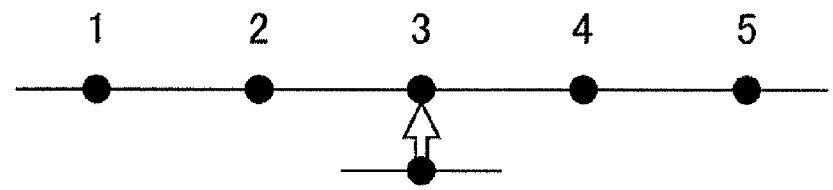
FIG. 10A is a first diagram illustrating an example of a case where an operational state is corrected by the identified activity correction unit in the control unit of the activity meter according to the embodiment.
Figure 10B:
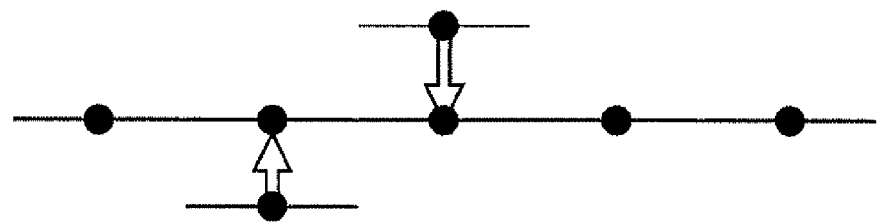
FIG. 10B is a second diagram illustrating an example of a case where the operational state is corrected by the identified activity correction unit in the control unit of the activity meter according to the embodiment.

FIG. 10A is a first diagram illustrating an example of a case where the operational state is corrected by the identified activity correction unit 115 in the control unit 110 of the activity meter 100 according to this embodiment. FIG. 10B is a second diagram illustrating an example of a case where the operational state is corrected by the identified activity correction unit 115 in the control unit 110 of the activity meter 100 according to this embodiment. As shown in FIG. 10A, the operational states of the first step and the fifth step are the same and an operational state that is different from the operational state in the first step and the fifth step and that is one step (the third step), which is less than 2.5 steps (greater than or equal to one step), is included, and thus this operational state transition is an abnormal transition.

Accordingly, this abnormal transition is corrected to a non-abnormal transition, in which the operational states are the same in the first step and the fifth step and the operational states contained in that range are the same. In other words, the operational state of the third step is corrected to be the same operational state as that in the first, second, fourth, and fifth steps.

Meanwhile, as shown in FIG. 10B, the operational states of the first step and the fifth step are the same and an operational state that is different from the operational state in the first step and the fifth step and that is two steps (the second step and the third step), which is less than 2.5 steps (greater than or equal to one step), is included, and thus this operational state transition is an abnormal transition.

Accordingly, this abnormal transition is corrected to a non-abnormal transition, in which the operational states are the same in the first step and the fifth step and the operational states contained in that range are the same. In other words, the operational states of the second step and the third step are corrected to be the same operational state as that in the first, fourth, and fifth steps.

Figure 11A:
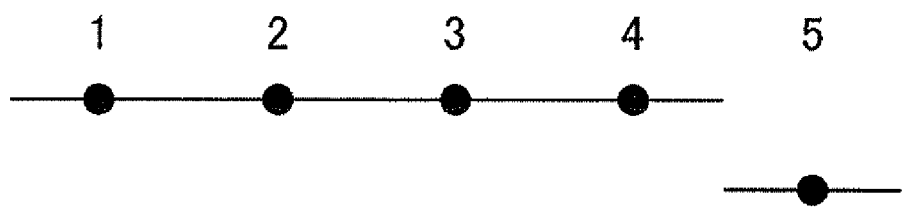
FIG. 11A is a first diagram illustrating an example of a case where an operational state is not corrected by the identified activity correction unit in the control unit of the activity meter according to the embodiment.
Figure 11B:
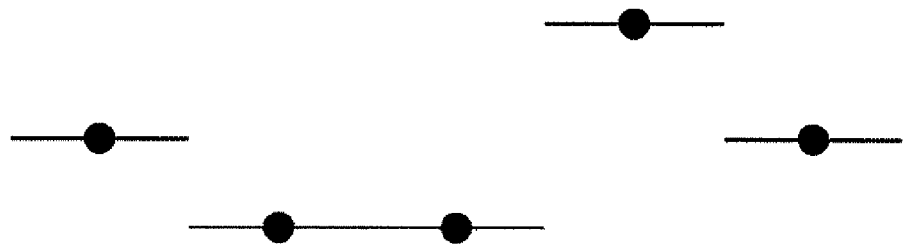
FIG. 11B is a second diagram illustrating an example of a case where the operational state is not corrected by the identified activity correction unit in the control unit of the activity meter according to the embodiment.

FIG. 11A is a first diagram illustrating an example of a case where the operational state is not corrected by the identified activity correction unit 115 in the control unit 110 of the activity meter 100 according to this embodiment. FIG. 11B is a second diagram illustrating an example of a case where the operational state is not corrected by the identified activity correction unit 115 in the control unit 110 of the activity meter 100 according to this embodiment. As shown in FIG. 11A, the operational states in the first step and the fifth step are not the same, and thus this operational state transition is not an abnormal transition. Accordingly, no correction is made.

Meanwhile, as shown in FIG. 11B, the operational states of the first step and the fifth step are the same, but an operational state that is different from the operational states in the first step and the fifth step and that is three steps (the second through fourth steps), which is greater than or equal to 2.5 steps, is included, and thus this operational state transition is not an abnormal transition. Accordingly, no correction is made.

Figure 12:
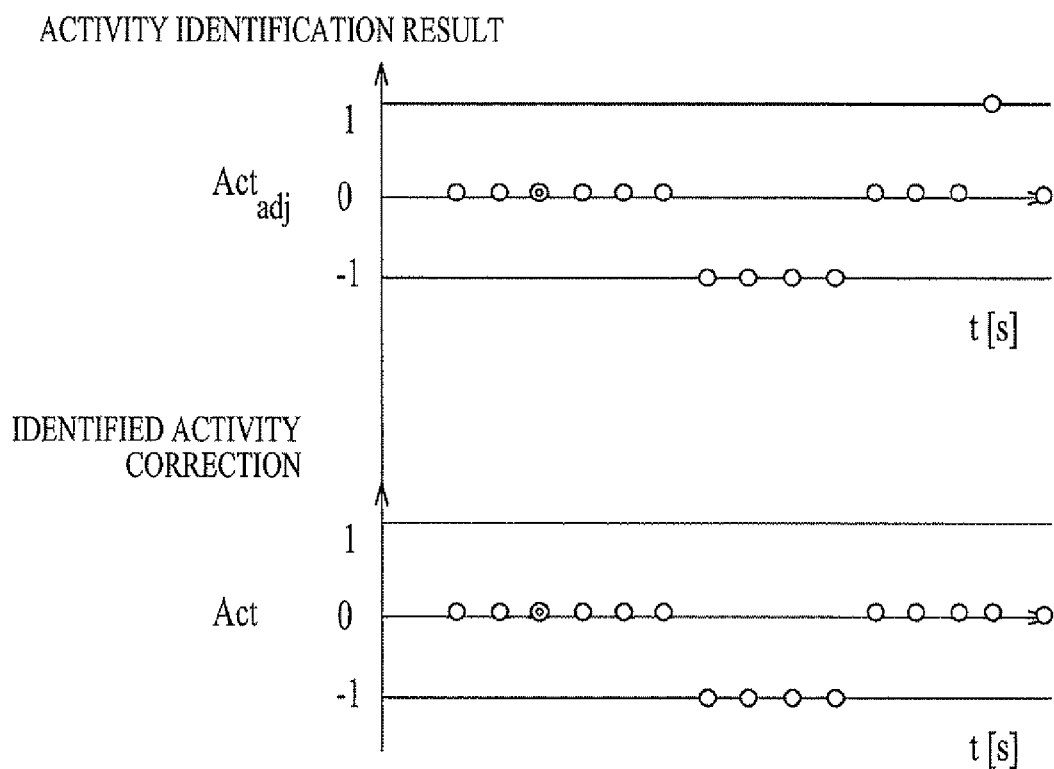
FIG. 12 is a graph illustrating an example of processes carried out by the identified activity correction unit in the control unit of the activity meter according to the embodiment.

FIG. 12 is a graph illustrating an example of processes carried out by the identified activity correction unit 115 in the control unit 110 of the activity meter 100 according to this embodiment. As shown in FIG. 12, the horizontal axis of the two graphs represents a time t (s). The graph on the first level is the same as the graph on the third level in FIG. 6.

The vertical axis of the graph on the second level expresses changes in an operational state identification correction result Act. In the graph on the first level, the operational states of the first step and the fifth step are the same for the first through fifth and second through sixth plots, and because an operational state that is different from the operational states of the first step and the fifth step is not present, there is no abnormal transition. Accordingly, no correction is made. Therefore, the value of the ascending/descending state identification result $Act_{adj}$ is used as-is for the value of the operational state identification correction result Act.

In the graph on the first level, the operational states of the first step and the fifth step are different for the third through seventh, fourth through eighth, fifth through ninth, sixth through tenth, seventh through eleventh, eighth through twelfth, ninth through thirteenth, and tenth through fourteenth plots, and thus there is no abnormal transition. Accordingly, no correction is made. Therefore, the value of the ascending/descending state identification result $Act_{adj}$ is used as-is for the value of the operational state identification correction result Act.

In the graph on the first level, with respect to the eleventh through fifteenth plots, the operational states of the first step and the fifth step are the same and an operational state that is different from the operational states of the first step and the fifth step and that is one step (the fourth step), which is less than 2.5 steps (greater than or equal to one step), is included, and thus there is an abnormal transition.

Accordingly, this abnormal transition is corrected to a non-abnormal transition, in which the operational states are the same in the first step and the fifth step and the operational states contained in that range are the same. In other words, the operational state of the fourth step (the fourteenth plot) is corrected to "0", which is the same operational state as those in the first through third and fifth steps (the eleventh through thirteenth and fifteenth plots), or in other words, to "walking on level ground". Therefore, the value of the ascending/descending state identification result $Act_{adj}$ is corrected and then used as the value of the operational state identification correction result Act.

The exercise intensity evaluation unit 116 specifies an exercise intensity in accordance with the operational states in the respective target judgment timings specified by the identified activity correction unit 115. Specifically, for example, it is assumed that the exercise intensities of ascending stairs, walking on level ground, and descending stairs are 8.0 METs, 3.0 METs, and 3.0 METs, respectively, based on the content of the reference ("Exercise Guide for Health Promotion 2006", published July, 2006, by the Exploratory Commission for the Establishment of Required Exercise Amounts and an Exercise Guide). Stopped (standing) and ascending/descending via automatic machine are assumed to be 1.2 METs each.

In the case where the exercise intensities of the operational states specified by the exercise intensity evaluation unit 116 are taken as $E_S$ (METs) and the duration times of the respective operational states are taken as $E_T$ (hours), the exercise amount evaluation unit 117 calculates an exercise amount $E_V$ per predetermined cycle (for example, one minute), based on a formula: exercise amount $E_V$ (exercise (Ex))=$\Sigma(E_S \times E_T)$. The calculated exercise amount $E_V$ is stored in the memory 120. In addition, the exercise amount $E_V$ is read out from the memory 120 and displayed in the display unit 140.

Figure 13:
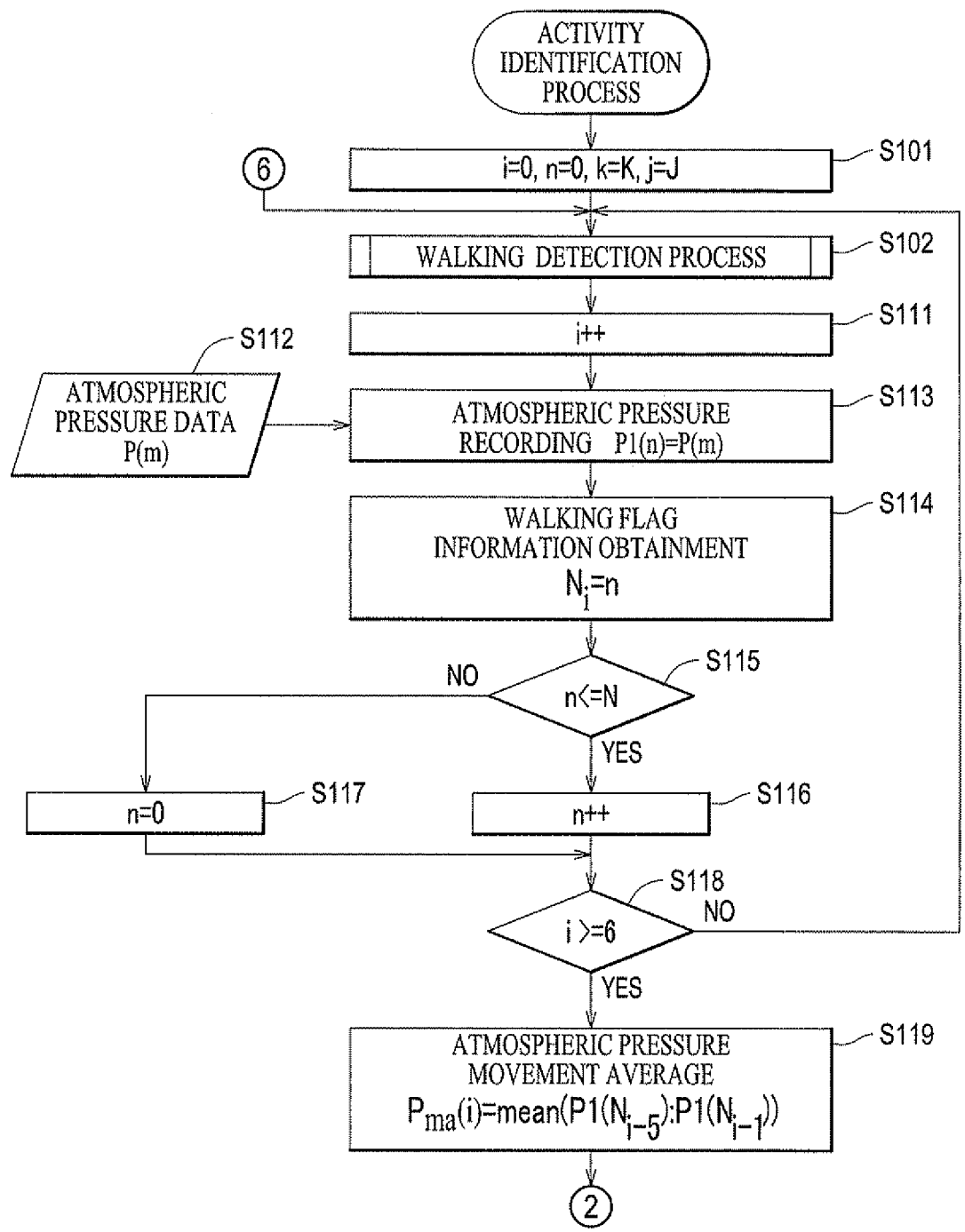
FIG. 13 is a first flowchart illustrating the flow of an activity identification process executed by the control unit of the activity meter according to the embodiment.

FIGS. 13 through 17 are first through fifth flowcharts illustrating the flow of an activity identification process executed by the control unit 110 of the activity meter 100 according to the embodiment. As shown in FIG. 13, first, in step S101, the control unit 110 of the activity meter 100 sets default values of variables i, n, k, and j to 0, 0, K, and J, respectively.

Here, the variable i expresses a number of steps. The variable n expresses the number of atmospheric pressure recorded data Pl(n), discussed later. The variable k expresses the number of a temporary holding variable $D_{diff}(k)$ for an atmospheric pressure change identification result. The constant K expresses the memory size of $D_{diff}(k)$. The variable j expresses the number of a temporary holding variable $D_{adj}(j)$ for an ascending/descending state identification result. The constant J expresses the memory size of $D_{adj}(j)$.

Next, in step S102, the control unit 110 executes a walking detection process. The following processing is carried out in the walking detection process. The control unit 110 detects walking of the user that is wearing or carrying the activity meter 100 based on acceleration values from the accelerometer 170. The walking detection is repeated in the case where walking has not been detected. The walking detection process ends in the case where a single step of walking has been detected.

In step S111, the control unit 110 adds 1 to the value of the variable i. Next, in step S112, the control unit 110 loads atmospheric pressure data from the atmospheric pressure sensor 180 to the a variable P(m). Note that each time the atmospheric pressure data P(m) is loaded, 1 is added to the value of the variable m, and when the memory size of the atmospheric pressure data P(m) has been reached, the atmospheric pressure data is loaded with 0 substituted for m.

In step S113, the control unit 110 substitutes the value of the atmospheric pressure data P(m) for the atmospheric pressure recorded data Pl(n). In step S114, the control unit 110 substitutes the value of the variable n for a walking flag obtainment time number $N_i$.

In step S115, the control unit 110 determines whether or not the value of the variable n is less than or equal to a constant N (n≤N). The constant N indicates the memory size of the atmospheric pressure recorded data Pl(n). If n≤N (YES in step S115), in step S116, the control unit 110 adds 1 to the value of the variable n. If n>N (NO in step S115), in step S117, the control unit 110 resets the value of the variable n to 0.

Through this, each time the value of the atmospheric pressure data P(m) is substituted for the atmospheric pressure recorded data Pl(n), 1 is added to the value of the variable n, and when the memory size of the atmospheric pressure recorded data Pl(n) has been reached, the value of the atmospheric pressure data P(m) is substituted again starting with n=0.

After step S116 and step S117, in step S118, the control unit 110 determines whether or not the value of the variable i is greater than or equal to 6 (i≥6). If i<6 (NO in step S118), the control unit 110 returns the processing being executed to the process in step S102. However, if i≥6 (YES in step S118), in step S119, the control unit 110 calculates a smoothed atmospheric pressure $P_{ma}(i)=mean(Pl(N_{i-5}):Pl(N_{i-1}))$.

Note that in the aforementioned FIG. 4, the average value of atmospheric pressure values in a five-step range from two steps before to two steps after the target judgment timing is taken as the smoothed atmospheric pressure $P_{ma}$. However, the activity identification process indicated in this flowchart is a real-time process in which the timing at which a corrected operational state for walking at a given timing is obtained is prior to the timing of the next walking, and thus an average value of the atmospheric pressure values in a five-step range from five steps before to one step before the target judgment timing is taken as a smoothed atmospheric pressure $P_{ma}(i)$.

Figure 14:
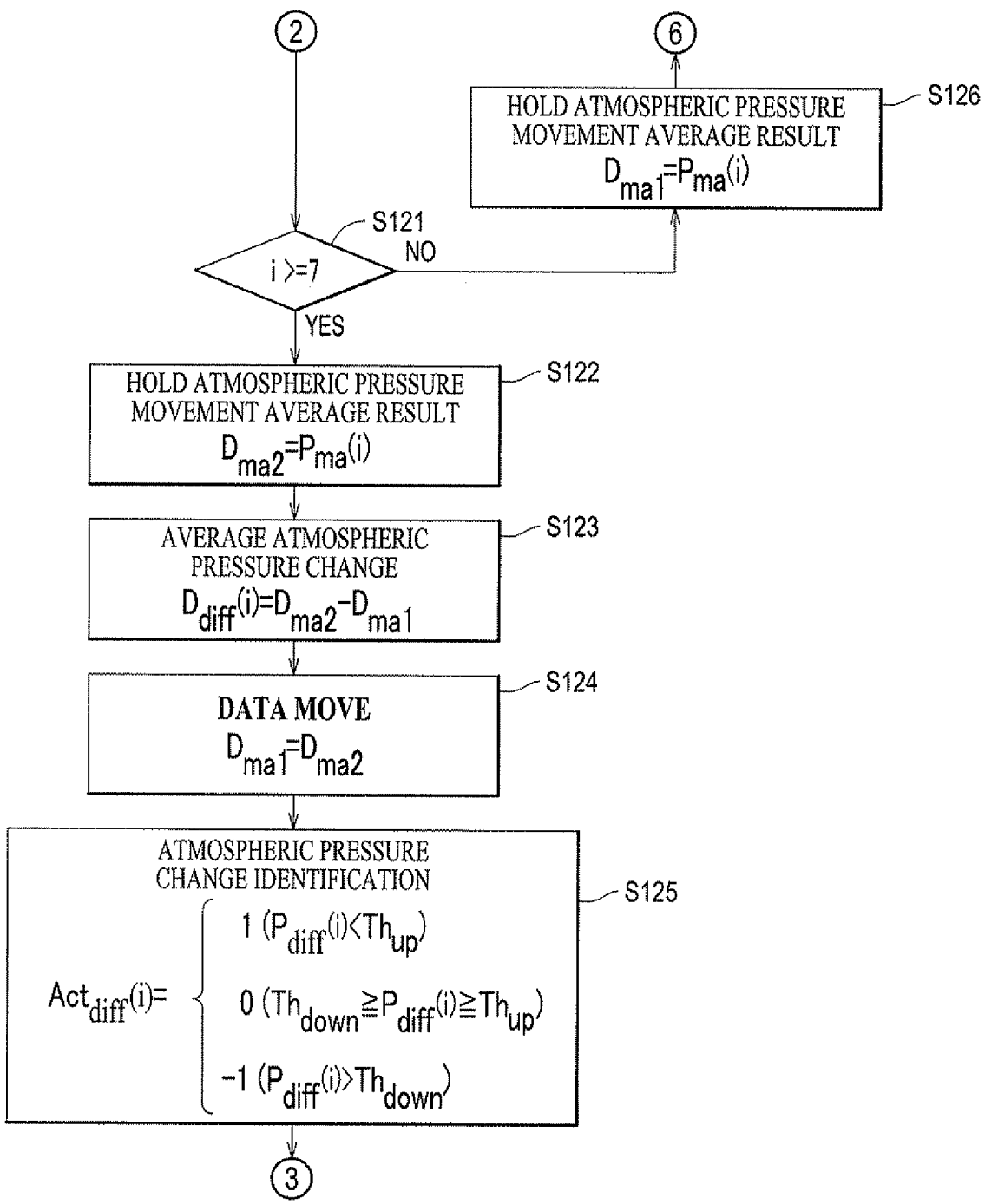
FIG. 14 is a second flowchart illustrating the flow of the activity identification process executed by the control unit of the activity meter according to the embodiment.

As shown in FIG. 14, after step S118, in step S121, the control unit 110 determines whether or not the value of the variable i is greater than or equal to 7 (i≥7). If i<7 (NO in step S121), in step S126, the control unit 110 holds the value of the smoothed atmospheric pressure $P_{ma}(i)$ in a temporary holding variable $D_{ma1}$ for the smoothed atmospheric pressure, and returns the executed processing to the process in step S102 of FIG. 13.

On the other hand, if i≥7 (YES in step S121), in step S122, the control unit 110 holds the value of the smoothed atmospheric pressure $P_{ma}(i)$ in a temporary holding variable $D_{ma2}$ for the smoothed atmospheric pressure. Then, in step S123, the control unit 110 calculates a change amount $P_{diff}(i)$, from the smoothed atmospheric pressure one step before the target judgment timing to the smoothed atmospheric pressure at the target judgment timing, as $D_{ma2}-D_{ma1}$.

Next, in step S124, the control unit 110 moves the value of the temporary holding variable $D_{ma2}$ for the smoothed atmospheric pressure to the temporary holding variable $D_{ma1}$ for the smoothed atmospheric pressure.

Next, in step S125, the control unit 110 determines the value of an atmospheric pressure change identification result $Act_{diff}(i)$ in accordance with the value of the change amount $P_{diff}(i)$ at the target judgment timing. Specifically, in the case where $P_{diff}(i)<Th_{up}$, the value of $Act_{diff}(i)$ is set to 1. In the case where $Th_{up} \le P_{diff}(i) \le Th_{down}$, the value of $Act_{diff}(i)$ is set to 0. In the case where $P_{diff}(i)>Th_{down}$, the value of $Act_{diff}(i)$ is set to −1.

Figure 15:
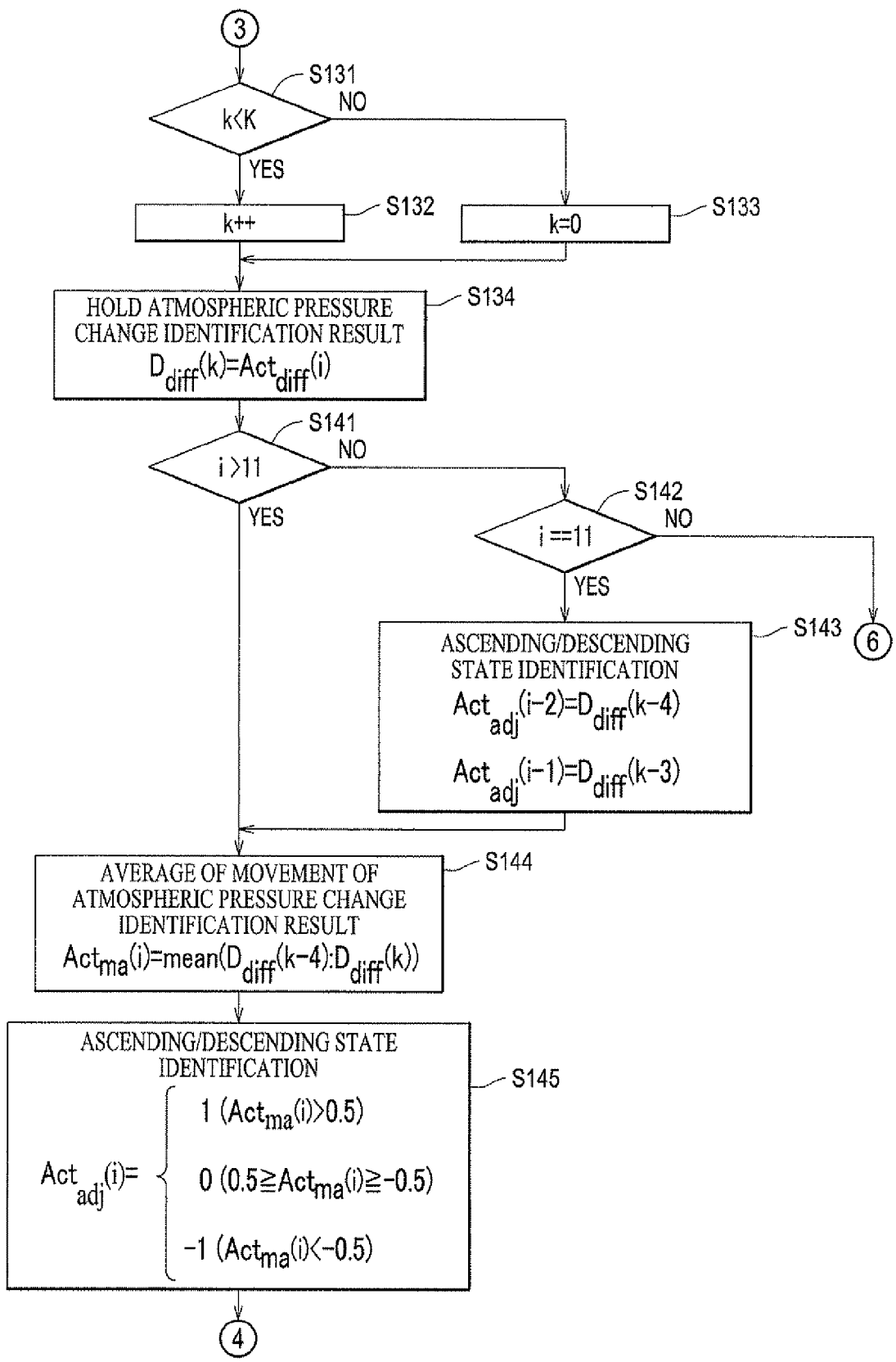
FIG. 15 is a third flowchart illustrating the flow of the activity identification process executed by the control unit of the activity meter according to the embodiment.

As shown in FIG. 15, after step S125, in step S131, the control unit 110 determines whether or not the value of the variable k is lower than the constant K (k<K). If k≤K (YES in step S131), in step S132, the control unit 110 adds 1 to the value of the variable k. If k≥K (NO in step S131), in step S133, the control unit 110 resets the value of the variable k to 0.

After step S132 and step S133, in step S134, the value of the atmospheric pressure change identification result $Act_{diff}(i)$ is held in the temporary holding variable $D_{diff}(k)$ for the atmospheric pressure change identification result.

Through this, each time the value of the atmospheric pressure change identification result $Act_{diff}(i)$ is substituted for the temporary holding variable $D_{diff}(k)$ for the atmospheric pressure change identification result, 1 is added to the value of the variable k, and in the case where the memory size of the temporary holding variable $D_{diff}(k)$ for the atmospheric pressure change identification result has been reached, the value of atmospheric pressure change identification result $Act_{diff}(i)$ is substituted again starting with k=0.

Next, in step S141, the control unit 110 determines whether or not the value of the variable i is greater than 11 (i>11). If i≤11 (NO in step S141), in step S142, the control unit 110 determines whether or not i is 11 (i=11). If the value of the variable i is not 11 (NO in step S142), the control unit 110 returns the processing being executed to step S102 in FIG. 13.

On the other hand, if the value of the variable i is 11 (YES in step S142), in step S143, the control unit 110 substitutes the value of a temporary holding variable $D_{diff}(k-4)$ of the atmospheric pressure change identification result for an ascending/descending state identification result $Act_{adj}(i-2)$. In addition, the value of a temporary holding variable $D_{diff}(k-3)$ of the atmospheric pressure change identification result is substituted for an ascending/descending state identification result $Act_{adj}(i-1)$.

After step S143, and in the case where i>11 (YES in step S141), in step S144, the identification result movement average $Act_{ma}(i)$ is calculated as mean($D_{diff}(k-4):D_{diff}(k)$).

Note that in the aforementioned FIG. 4, the average value in a five-step range from two steps before to two steps after the target judgment timing is taken as the identification result movement average $Act_{ma}$. However, the activity identification process indicated in this flowchart is a real-time process in which the timing at which a corrected operational state for walking at a given timing is obtained is prior to the timing of the next walking, and thus an average value of the atmospheric pressure change identification result values in a five-step range from four steps before the target judgment timing to that timing is taken as the identification result movement average $Act_{ma}(i)$.

Next, in step S145, the control unit 110 determines the value of the ascending/descending state identification result $Act_{adj}(i)$ in accordance with the value of the identification result movement average $Act_{ma}(i)$ at the target judgment timing. Specifically, in the case where $Act_{ma}(i) > 0.5$, the value of $Act_{adj}(i)$ is set to 1. In the case where $0.5 \geq Act_{ma}(i) \geq -0.5$, the value of $Act_{adj}(i)$ is set to 0. In the case where $Act_{ma}(i) < -0.5$, the value of $Act_{adj}(i)$ is set to −1.

Figure 16:
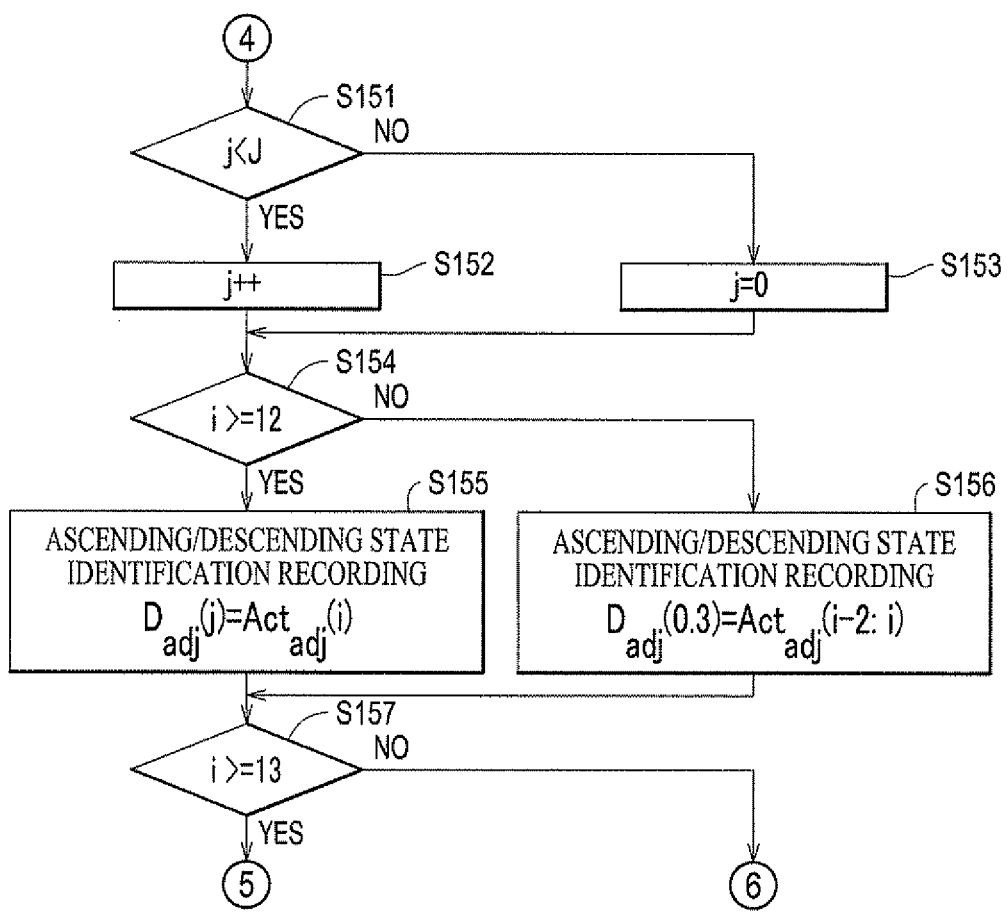
FIG. 16 is a fourth flowchart illustrating the flow of the activity identification process executed by the control unit of the activity meter according to the embodiment.

As shown in FIG. 16, after step S145, in step S151, the control unit 110 determines whether or not the value of the variable j is lower than the constant J (j<J). If j≤J (YES in step S151), in step S152, the control unit 110 adds 1 to the value of the variable j. If j≥J (NO in step S151), in step S153, the control unit 110 resets the value of the variable j to 0.

After step S152 and step S153, in step S154, the control unit 110 determines whether or not the value of the variable i is greater than or equal to 12 (i≥12). If i<12 (NO in step S154), in step S156, the control unit 110 substitutes the values of the ascending/descending state identification result $Act_{adj}(i-2)$ through $Act_{adj}(i)$ for temporary holding variables $D_{adj}(0)$ through $D_{adj}(3)$ of the ascending/descending state identification result, respectively.

However, if i≥12 (YES in step S154), in step S155, the control unit 110 substitutes the value of the ascending/descending state identification result $Act_{adj}(i)$ for the temporary holding variable $D_{adj}(j)$ of the ascending/descending state identification result.

Through this, each time the value of the ascending/descending state identification result $Act_{adj}(i)$ is substituted for the temporary holding variable $D_{adj}(j)$ of the ascending/descending state identification result, 1 is added to the value of the variable j, and in the case where the memory size of the temporary holding variable $D_{adj}(j)$ of the ascending/descending state identification result is reached, the value of the ascending/descending state identification result $Act_{adj}(i)$ is substituted again starting with j=0.

After step S155 and step S156, in step S157, the control unit 110 determines whether or not the value of the variable i is greater than or equal to 13 (i≥13). If i<13 (NO in step S157), the control unit 110 returns the processing being executed to the process in step S102 shown in FIG. 13. However, if i≥13 (YES in step S157), the control unit 110 advances the processing being executed to the process in step S161 shown in FIG. 17.

Figure 17:
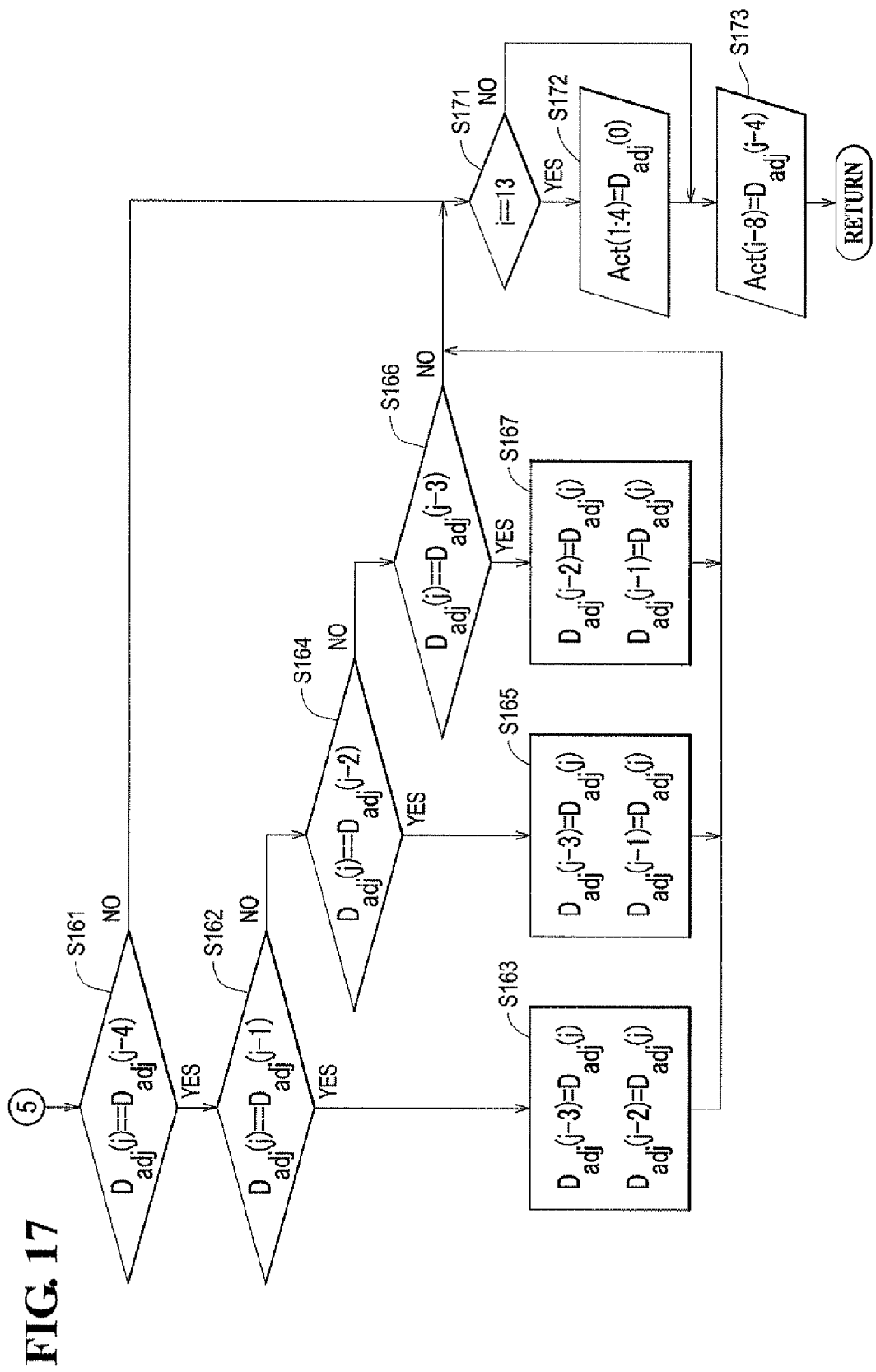
FIG. 17 is a fifth flowchart illustrating the flow of the activity identification process executed by the control unit of the activity meter according to the embodiment.

As shown in FIG. 17, in step S161, the control unit 110 determines whether or not the value of $D_{adj}(j)$ is equal to the value of $D_{adj}(j-4)$ (that is, $D_{adj}(j)=D_{adj}(j-4)$). In the case where the values have been determined not to be equal (NO in step S161), the control unit 110 advances the processing being executed to the process in step S171.

On the other hand, in the case where it has been determined that the value of $D_{adj}(j)$ and the value of $D_{adj}(j-4)$ are equal (YES in step S161), in step S162, the control unit 110 determines whether or not the value of $D_{adj}(j)$ is equal to the value of $D_{adj}(j-1)$ (that is, $D_{adj}(j)=D_{adj}(j-1)$).

In the case where it has been determined that the value of $D_{adj}(j)$ and the value of $D_{adj}(j-1)$ are equal (YES in step S162), in step S163, the control unit 110 sets the values of $D_{adj}(j-3)$ and $D_{adj}(j-2)$ to the value of $D_{adj}(j)$. Thereafter, the control unit 110 advances the processing being executed to the process in step S171.

In the case where it has been determined that the value of $D_{adj}(j)$ and the value of $D_{adj}(j-1)$ are not equal (NO in step S162), in step S164, the control unit 110 determines whether or not the value of $D_{adj}(j)$ is equal to the value of $D_{adj}(j-2)$ (that is, $D_{adj}(j)=D_{adj}(j-2)$).

In the case where it has been determined that the value of $D_{adj}(j)$ and the value of $D_{adj}(j-2)$ are equal (YES in step S164), in step S165, the control unit 110 sets the values of $D_{adj}(j-3)$ and $D_{adj}(j-1)$ to the value of $D_{adj}(j)$. Thereafter, the control unit 110 advances the processing being executed to the process in step S171.

In the case where it has been determined that the value of $D_{adj}(j)$ and the value of $D_{adj}(j-2)$ are not equal (NO in step S164), in step S166, the control unit 110 determines whether or not the value of $D_{adj}(j)$ is equal to the value of $D_{adj}(j-3)$ (that is, $D_{adj}(j)=D_{adj}(j-3)$).

In the case where it has been determined that the value of $D_{adj}(j)$ and the value of $D_{adj}(j-3)$ are equal (YES in step S166), in step S167, the control unit 110 sets the values of $D_{adj}(j-2)$ and $D_{adj}(j-1)$ to the value of $D_{adj}(j)$. Thereafter, the control unit 110 advances the processing being executed to the process in step S171.

In step S171, the control unit 110 determines whether or not the value of the variable i is 13 (i=13). If i=13 (YES in step S171), in step S172, the control unit 110 substitutes the value of the temporary holding variable $D_{adj}(0)$ of the ascending/descending state identification result for the operational state identification correction result Act(1) through (4).

In the case where it has been determined that i is not equal to 13 (NO in step S171), and after step S172, in step S173, the control unit 110 substitutes the value of the temporary holding variable $D_{adj}(j-4)$ of the ascending/descending state identification result for the operational state identification correction result Act(i−8). Thereafter, the control unit 110 returns the processing being executed to the call origin of the activity identification process.

Method for Determining Thresholds $Th_{up}$ and $Th_{down}$

Next, a method for determining the aforementioned thresholds $Th_{up}$ and $Th_{down}$ will be described. First, data indicating changes in atmospheric pressure values is measured and recorded for multiple men and women wearing the aforementioned atmospheric pressure sensor 180 of the activity meter 100, in the case where those users have carried out various types of walking such as walking on level ground, ascending stairs, descending stairs, and so on. In addition, the operational states (walking on level ground, ascending stairs, or descending stairs) is also observed and recorded at the respective walking timings. Based on these recorded values, the smoothed atmospheric pressure change amount $P_{diff}$ is calculated for each step for the various types of walking.

In order to determine and test the thresholds for judging the operational state, data indicating changes in the identification rate of the operational states is obtained while changing the thresholds. The identification rate of ascending stairs for each threshold is calculated through the following equation: identification rate of ascending stairs (%)=(number of instances of data of smoothed atmospheric pressure change amount $P_{diff}$ identified as ascending stairs using that threshold)/(number of instances of data of smoothed atmospheric pressure change amount $P_{diff}$ when actually ascending stairs). Note that the data of the smoothed atmospheric pressure change amount $P_{diff}$ identified as ascending stairs using that threshold is data that, when the value of the threshold is taken as $Th_n$, fulfills the relationship $P_{diff} > Th_n$. The identification rate of ascending stairs increases monotonically as the threshold $Th_n$ is increased from −0.1, and reaches 100% slightly after the threshold has exceeded 0.

The identification rate of walking on level ground for each threshold is calculated through the following equation: identification rate of walking on level ground (%)=(number of instances of data of smoothed atmospheric pressure change amount $P_{\mathit{diff}}$ identified as walking on level ground using that threshold)/(number of instances of data of smoothed atmospheric pressure change amount $P_{\mathit{diff}}$ when actually walking on level ground). Note that the data of the smoothed atmospheric pressure change amount $P_{\mathit{diff}}$ identified as walking on level ground using that threshold is data that, when the value of the threshold is taken as $Th_n$, fulfills the relationship $-|Th_n| \leq P_{\mathit{diff}} \leq |Th_n|$. The identification rate of walking on level ground increases monotonically as the threshold $|Th_n|$ is increased from 0.01, and reaches 100% slightly after the threshold has exceeded 0.1.

Based on the identification rate of ascending stairs and the identification rate of walking on level ground at a given threshold, the threshold $Th_{up}$ at which the respective identification rates are optimal can be determined. In this range ($Th_{up} > 0$), the identification rate of ascending stairs increases as the threshold $Th_{up}$ increases, but conversely, the identification rate of walking on level ground decreases. Accordingly, the respective identification rates may simply be plotted on a graph, and the point of intersection between the two may simply be determined as the threshold $Th_{up}$. $Th_{down}$ can be determined in the same manner.

FIG. 18 is a graph illustrating an identification rate for the operational state when using a threshold during the determination and testing of a threshold for judging the operational state. As shown in FIG. 18, the identification rate of the operational state found by carrying out correction is exponentially improved compared to a case where only the atmospheric pressure is used and correction is not carried out; in all situations, an identification rate of 90% or more is obtained.

CONCLUSION (1) As described above, the activity meter 100 according to the present embodiment includes the main body unit 191, the control unit 110, the memory 120, and the accelerometer 170 and atmospheric pressure sensor 180 that detect values indicating the displacement of the main body unit 191. According to the activity meter 100, in a judgment process, in which the operational state of a user that wears or carries the main body unit 191 is judged based on values detected by the accelerometer 170 and the atmospheric pressure sensor 180 at a given target judgment timing, a correction is carried out on the data from the judgment process based on a predetermined rule as illustrated in FIGS. 10 and 11 using the values present in timings before and after the target judgment timing of detection; the operational state is then judged, and the judged operational state is stored in the memory 120. Through this, it is possible to reduce erroneous judgments of the user's operational state.

(2) Furthermore, as illustrated in FIGS. 10 and 11, the predetermined rule is a rule that, when the operational state has transited between the target judgment timing and the timings before and after that timing, corrects an abnormal transition, which is a transition that is different from a possible transition, to a non-abnormal transition. Through this, it is possible to correct an operational state transition that is abnormal to an operational state transition that is not abnormal.

(3) Furthermore, with respect to the operational states in each step in a range of two steps before and after the target judgment timing, an abnormal transition is a transition in which the operational states of the first step and the fifth step are the same and an operational state that is different from the operational states in the first step and the fifth step and that is less than 2.5 steps is present, whereas a non-abnormal transition is a transition in which the operational states of the first step and the fifth step are the same and the operational states in that range are all the same.

(4) In addition, the operational state is a combination of a walking state, indicating whether or not the user is walking, and an ascending/descending state, indicating whether the user is ascending, descending, or not ascending/descending.

(5) In addition, acceleration values in each of three axial directions are detected by the accelerometer 170, and in the judgment process, the walking state of the user's operational states is judged based on the acceleration values detected by the accelerometer 170.

(6) In addition, absolute pressure values are detected by the atmospheric pressure sensor 180, and in the judgment process, the ascending/descending state of the user's operational states is judged based on the absolute pressure values detected by the atmospheric pressure sensor 180.

(7) In addition, the target judgment timing and the timings before and after the timing are the timings of each step, which is a unit of walking. Accordingly, the operational state can be corrected for each step of walking.

(8) The target judgment timing and the timings before and after that timing are, in the case where walking is not detected, timings of each predetermined amount of time T (for example, 1) seconds. Accordingly, the operational state can be corrected even in the case where walking is not detected.

(9) In addition, an exercise intensity $E_S$ (METs) is specified based on operational states recorded in the memory 120, and an exercise amount $E_V$ is calculated using duration times $E_T$ (hours) of each of the operational states recorded in the memory 120 and the specified exercise intensity $E_S$ (exercise $(Ex)) = \Sigma(E_S \times E_T)$.

Next, variations on the aforementioned embodiment will be described.

(1) In the aforementioned embodiment, the operational state is corrected according to the rules illustrated in FIGS. 10 and 11. However, the correction is not limited thereto, and may be carried out as follows.

As illustrated in FIGS. 8 and 9, there are operational states that are absolutely not transited to from a given operational state. For example, the operational states of ascending on an escalator or descending on an escalator do not transit to the operational states of stopped, ascending/descending stairs, and ascending/descending in an elevator.

Accordingly, in a case where, after several steps or an amount of time several times longer than the predetermined amount of time T second from the timing judged to have an operational state of ascending on an escalator, a timing at which an operational state of stopped, ascending/descending stairs, or ascending/descending in an elevator is judged, and then an operational state of ascending on an escalator is once again judged, operational state during that period may be corrected to the operational state of ascending on an escalator.

In other words, in the case where the first and last operational states at timings in a given range are the same, and an operational state to which the first and last operational state does not transit is present as an operational state at a timing therebetween, the operational states may be corrected according to a rule that states that the first and last operational states are corrected.

(2) In the aforementioned embodiment, the operational states of the respective target judgment timings specified by the identified activity correction unit 115 may be displayed in the display unit 140.

(3) The aforementioned embodiment describes the activity meter 100 as an apparatus invention. However, the invention is not limited thereto, and can also be taken as a control method invention for controlling the activity meter 100.

(4) Note that the embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

REFERENCE SIGNS LIST

100 activity meter
110 control unit
111 walking detection unit
112 atmospheric pressure smoothing unit
113 atmospheric pressure change amount evaluation unit
114 activity evaluation unit
115 identified activity correction unit
116 exercise intensity evaluation unit
117 exercise amount evaluation unit
120 memory
130 operation unit
131 display toggle/OK switch
132 left operation/memory switch
133 right operation switch
140 display unit
141 display
170 accelerometer
180 atmospheric pressure sensor
190 power source
191 main body unit
192 clip unit

The invention claimed is:

1. An exercise detection apparatus that is configured to be worn or carried by a user, the exercise detection apparatus comprising:
  a main body unit, the main body unit including a display unit and a display switch;
  a storage unit;
  a detection unit; and
  a control unit configured to:
    judge whether predetermined movements of a body of the user are occurring based on data detected by the detection unit;
    judge a movement state for the body across a predetermined unit of body movements based on data detected by the detection unit;
    calculate an exercise state of the user during the predetermined unit of body movements based on the respective judgment results;
    store the exercise state calculated by the control unit in the storage unit; and
    correct a target exercise state based on a predetermined rule, wherein
      the predetermined rule is a rule for correcting the target exercise state based on a transition of the exercise state;
      the transition occurs between the target exercise state and exercise states before and after the target exercise state; and
      the display unit displays the corrected target exercise state.

2. The exercise detection apparatus according to claim 1, wherein the predetermined rule is a rule that, for transitions of the exercise state between the target exercise state and the exercise states before and after the target exercise state, corrects an abnormal transition to a non-abnormal transition.

3. The exercise detection apparatus according to claim 2, wherein
  for the exercise states calculated by the control unit for each unit of body movements in a range of a predetermined number of units of body movements from before to after the unit of body movements that is the target of the exercise state calculation,
  the abnormal transition is a transition in which the exercise states of the first and last units of body movements in the range are the same, and exercise states that differ from the exercise states of the first and last units of body movements in the range make up less than half of the exercise states of units of body movements in the range, and
  the non-abnormal transition is a transition in which the exercise states of the first and last units of body movements in the range are the same and the exercise states of the other units of body movements in the range are the same.

4. The exercise detection apparatus according to claim 1, wherein the exercise state is a function of both the identity of the movements of the body and the movement state.

5. The exercise detection apparatus according to claim 1, wherein
  the detection unit detects an acceleration value in at least one axial direction; and
  the control unit judges whether predetermined movements of the body are occurring based on the acceleration value detected by the detection unit.

6. The exercise detection apparatus according to claim 1, wherein
  the detection unit detects absolute pressure values; and
  the control unit judges the movement state based on the absolute pressure values detected by the detection unit.

7. The exercise detection apparatus according to claim 1, wherein the control unit is further configured to:
  specify an exercise intensity based on the exercise states stored in the storage unit; and
  calculate an exercise amount using duration times of the exercise states stored in the storage unit and the exercise intensities of the respective stored exercise states specified by the control unit.

8. A control method for an exercise detection apparatus that is configured to be worn or carried by a user, the exercise detection apparatus including a main body unit having a display unit and a display switch, a control unit, a storage unit, and a detection unit, wherein the control unit is configured to execute the control method comprising:
  a step of judging whether predetermined movements of a body of a user are occurring based on data detected by the detection unit;
  a step of judging a movement state for the body across a predetermined unit of body movements based on data detected by the detection unit;
  a step of calculating an exercise state of the user based on a result of the judging steps;
  a step of storing the calculated exercise state in the storage unit; and
  a step of correcting a target exercise state based on a predetermined rule, wherein
    the predetermined rule is a rule for correcting the target exercise state based on a transition of the exercise state;

the transition occurs between the target exercise state and exercise states before and after the target exercise state; and the display unit displays the corrected target exercise state.

9. The method according to claim 8, wherein the control unit method further comprises:

a step of specifying an exercise intensity of the exercise states stored in the storage unit; and a step of calculating an exercise amount using duration times of the exercise states stored in the storage unit and the specified exercise intensities of the respective stored exercise states.

10. The method according to claim 9, wherein the exercise amount is displayed to a user who is wearing or carrying the exercise detection unit.

11. The exercise detection apparatus according to claim 7, wherein the display unit displays the exercise amount, and is contained in a housing with the detection unit.

* * * * *